United States Patent [19]
Vuligonda et al.

[11] Patent Number: 6,087,505
[45] Date of Patent: Jul. 11, 2000

[54] BENZO[1,2-G]-CHROM-3-ENE, AND BENZO [1,2-G]-THIOCHROM-3-ENE DERIVATIVES

[75] Inventors: Vidyasagar Vuligonda, Irvine; Alan T. Johnson, Rancho Santa Margarita; Roshantha A. Chandraratna, Mission Viejo, all of Calif.

[73] Assignee: Allergan Sales, Inc., Irvine, Calif.

[21] Appl. No.: 09/030,350

[22] Filed: Feb. 25, 1998

Related U.S. Application Data

[62] Division of application No. 08/764,466, Dec. 12, 1996, Pat. No. 5,728,846.

[51] Int. Cl.$^7$ .................................................. C07D 401/00
[52] U.S. Cl. ................................... 546/281.1; 546/279.7; 546/281.7; 546/284.7; 546/268.1
[58] Field of Search ............................ 546/280.4, 283.4, 546/281.1, 284.1, 279.7, 281.7

[56] References Cited

U.S. PATENT DOCUMENTS

| | | | |
|---|---|---|---|
| 4,326,055 | 4/1982 | Loeliger | 542/429 |
| 4,391,731 | 7/1983 | Boller et al. | 252/299.26 |
| 4,485,252 | 11/1984 | Fuchs et al. | 560/8 |
| 4,539,154 | 9/1985 | Krebs | 260/410 |
| 4,723,028 | 2/1988 | Shudo | 560/8 |
| 4,826,984 | 5/1989 | Berlin et al. | 546/134 |
| 4,833,240 | 5/1989 | Maignana et al. | 536/55.2 |
| 4,923,884 | 5/1990 | Chandraratna | 514/354 |
| 4,927,947 | 5/1990 | Chandraratna | 549/484 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |

(List continued on next page.)

FOREIGN PATENT DOCUMENTS

| | | | |
|---|---|---|---|
| 170105 | of 0000 | European Pat. Off. . | |
| 0098591 | 1/1984 | European Pat. Off. | C07D 333/54 |
| 0130795 | 1/1985 | European Pat. Off. | C07D 311/58 |
| 0176032 | 4/1986 | European Pat. Off. | C07C 65/38 |
| 0176033 | 4/1986 | European Pat. Off. | C07D 261/18 |
| 0253302 | 1/1988 | European Pat. Off. | C07D 213/16 |
| 0272921 | 6/1988 | European Pat. Off. | C07D 213/80 |
| 0284261 | 9/1988 | European Pat. Off. | C07D 213/80 |
| 0284288 | 9/1988 | European Pat. Off. | C07D 401/04 |
| 0286364 | 10/1988 | European Pat. Off. | C07C 103/78 |
| 0303186 | 2/1989 | European Pat. Off. . | |
| 0303915 | 2/1989 | European Pat. Off. | A61K 31/255 |
| 0315071 | 5/1989 | European Pat. Off. | C07C 63/66 |
| 0412387 | 2/1991 | European Pat. Off. | C07C 317/14 |
| 0478787 | 10/1991 | European Pat. Off. | C07C 233/65 |
| 0514269 | 11/1992 | European Pat. Off. | C07C 257/08 |
| 0617020 | 9/1994 | European Pat. Off. | C07D 213/82 |
| 0619116 | 10/1994 | European Pat. Off. | A61K 31/19 |
| 0661259 | 5/1995 | European Pat. Off. | C07C 233/81 |
| 0661258 | 7/1995 | European Pat. Off. | C07D 65/19 |

(List continued on next page.)

OTHER PUBLICATIONS

Wierzbicki et al. (CA 88: 190510, abstract of Eur. J. Med. Chem.–Chim. THer. (1977), 12(6), 557–63), 1977.
A General Synthesis of Terminal and Internal Arylalkynes by the Palladium–Catalyzed Reaction of Alkynylzinc Reagents with Aryl Halides by Anthony O. King and Ei–i–chi, *J. Org. Chem.*, (1978) 43/2: p. 358.
Conversion of Methyl Ketones into Terminal Acetylenes and (E)–Tri–substituted Olefins of Terpenoid Origin by Ei–ichi, et al., *J. Org. Chem.*, (1980) 45/12: p. 2526.
Sporn et al. in *J. Amer. Acad. Derm* . . , (1986) 15:756–764.
Liu, S. S. et al. "Systemic Pharmacokinetics of Acetylenic Retinoids in Rats", *Drug Metabolism and Disposition*, (1990) 18/6: 1071–1077.
Chemical Abstracts, vol. 122, No. 13, Mar. 27, 1995 abstract No. 151372m, (S. Kaku et al.).
Chemical Abstracts, vol. 117, No. 13, Sep. 28, 1992 abstract No. 124091j, (S. Sun et al.).
European Journal of Biochemistry, vol. 212, No. 1, 1993, Berlin, pp. 13–26, XP000618300 (S. Keidel et al.).
Journal of Medicinal Chemistray, vol. 39, No. 16, Aug. 2, 1996, pp. 3035–3038, Min Teng et al.
Journal of Medicinal Chemistry, vol. 37, No. 10, May 13, 1994, pp. 1508–1517, Laurence Eyrolles.
Biochemical and Biophysical Research Communications, vol. 155 No. 1, 1988, pp. 503–508.
Chemical Abstracts. vol. 121, No. 9, 1994.
Database WPi Section CH, Week 9416, Derwent Publications Ltd. London, GB; Class B05, AN 94–128759 and JP 6078266A, see English language abstract in Derwent.
Journal of Medicinal Chemistry, vol. 38, No. 16, Aug. 4, 1995, pp. 3163–3173.
Weiner, et al., "A phase I trial of topically applied trans–retinoic acid in cervical dysplasia–clinical efficacy", *Investigational New Drugs*, 4:241–244, 1996.

(List continued on next page.)

*Primary Examiner*—Jose' G. Dees
*Assistant Examiner*—Sabiha Qazi
*Attorney, Agent, or Firm*—Gabor L. Szekeres; Robert J. Baran; Martin A. Voet

[57] ABSTRACT

Compounds of the formula

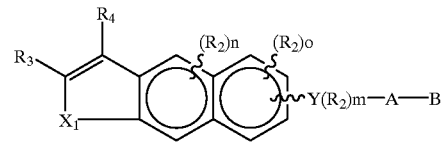

where the symbols have the meaning defined in the specification, have retinoid, retinoid antagonist and/or retinoid inverse-agonist-like biological activity.

3 Claims, No Drawings

U.S. PATENT DOCUMENTS

| | | | |
|---|---|---|---|
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,354,776 | 10/1994 | Chandratatna | 514/461 |
| 5,380,877 | 1/1995 | Chandraratna | 549/60 |
| 5,391,753 | 2/1995 | Chandraratna | 546/323 |
| 5,399,561 | 3/1995 | Chandraratna | 514/252 |
| 5,399,586 | 3/1995 | Davies et al. | 514/448 |
| 5,407,937 | 4/1995 | Chandraratna | 514/256 |
| 5,414,007 | 5/1995 | Chandraratna | 514/365 |
| 5,420,145 | 5/1995 | Shudo | 514/352 |
| 5,426,118 | 6/1995 | Chandraratna | 514/337 |
| 5,434,173 | 7/1995 | Chandraratna | 514/354 |
| 5,451,605 | 9/1995 | Chandraratna et al. | 514/475 |
| 5,455,265 | 10/1995 | Chandraratna | 514/448 |
| 5,466,861 | 11/1995 | Dawson et al. | 560/100 |
| 5,468,879 | 11/1995 | Chandraratna | 549/23 |
| 5,470,999 | 11/1995 | Chandraratna | 560/100 |
| 5,475,022 | 12/1995 | Chandraratna | 514/448 |
| 5,475,113 | 12/1995 | Chandraratna | 548/203 |
| 5,489,584 | 2/1996 | Vuligonda et al. | 514/188 |
| 5,498,755 | 3/1996 | Chandraratna et al. | 564/272 |
| 5,498,795 | 3/1996 | Song et al. | 562/474 |
| 5,514,825 | 5/1996 | Vuligonda et al. | 558/462 |
| 5,516,904 | 5/1996 | Chandraratna | 514/269 |
| 5,523,457 | 6/1996 | Starrett, Jr. et al. | 560/24 |
| 5,534,516 | 7/1996 | Chandraratna | 514/253 |
| 5,534,641 | 7/1996 | Song et al. | 549/416 |
| 5,543,534 | 8/1996 | Vuligonda et al. | 549/421 |
| 5,556,996 | 9/1996 | Beard et al. | 549/407 |
| 5,559,248 | 9/1996 | Starrett, Jr. et al. | 549/79 |
| 5,563,292 | 10/1996 | Sheh et al. | 560/255 |
| 5,591,858 | 1/1997 | Vuligonda et al. | 546/322 |
| 5,599,819 | 2/1997 | Chandraratna | 514/314 |
| 5,599,967 | 2/1997 | Vuligonda et al. | 560/48 |
| 5,602,130 | 2/1997 | Chandraratna | 514/247 |
| 5,602,135 | 2/1997 | Chandraratna | 514/252 |
| 5,605,915 | 2/1997 | Vuligond et al. | 514/356 |
| 5,616,597 | 4/1997 | Chandraratna | 514/365 |
| 5,616,712 | 4/1997 | Teng et al. | 546/158 |
| 5,618,836 | 4/1997 | Chandraratna et al. | 514/444 |
| 5,618,839 | 4/1997 | Starrett, Jr. et al. | 514/513 |
| 5,618,931 | 4/1997 | Beard et al. | 544/224 |
| 5,618,943 | 4/1997 | Vuligonda et al. | 546/342 |
| 5,619,936 | 4/1997 | Chandraratna et al. | 514/444 |
| 5,648,503 | 7/1997 | Vuligonda et al. | 549/13 |
| 5,648,514 | 7/1997 | Johnson et al. | 560/102 |
| 5,654,469 | 8/1997 | Vuligonda et al. | 560/56 |
| 5,663,347 | 9/1997 | Chandraratna | 546/152 |
| 5,663,357 | 9/1997 | Teng et al. | 546/323 |
| 5,663,367 | 9/1997 | Vuligonda et al. | 549/4 |
| 5,672,710 | 9/1997 | Beard et al. | 548/188 |
| 5,675,024 | 10/1997 | Teng et al. | 549/405 |
| 5,675,033 | 10/1997 | Vuligonda et al. | 560/100 |
| 5,677,320 | 10/1997 | Chandraratna | 514/365 |
| 5,677,323 | 10/1997 | Chandraratna | 514/374 |
| 5,677,451 | 10/1997 | Chandraratna | 544/238 |
| 5,688,957 | 11/1997 | Teng et al. | 546/280.1 |
| 5,696,162 | 12/1997 | Chandraratna | 514/532 |
| 5,698,700 | 12/1997 | Song et al. | 546/282.1 |
| 5,717,094 | 2/1998 | Chandraratna | 544/238 |
| 5,723,620 | 3/1998 | Vuligonda et al. | 546/280.1 |
| 5,723,666 | 3/1998 | Vuligonda et al. | 564/253 |
| 5,728,846 | 3/1998 | Vuligonda et al. | 549/16 |
| 5,739,338 | 4/1998 | Beard et al. | 546/153 |
| 5,741,896 | 4/1998 | Vuligonda et al. | 534/860 |
| 5,747,542 | 5/1998 | Vuligonda et al. | 514/646 |
| 5,750,693 | 5/1998 | Chandraratna | 544/253 |
| 5,760,276 | 6/1998 | Beard et al. | 560/102 |

FOREIGN PATENT DOCUMENTS

| | | | |
|---|---|---|---|
| 0661261 | 7/1995 | European Pat. Off. | C07C 235/84 |
| 0718285 | 8/1996 | European Pat. Off. | C07C 403/20 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3715955 | 11/1987 | Germany | C07C 15/58 |
| 2190378 | 11/1987 | United Kingdom | C07C 39/21 |
| 85/00806 | 2/1985 | WIPO | A61K 31/00 |
| 85/04652 | 10/1985 | WIPO | A61K 31/19 |
| 91/16051 | 10/1991 | WIPO | A61K 31/44 |
| 92/06948 | 4/1992 | WIPO | C07C 69/86 |
| 93/03713 | 3/1993 | WIPO | A61K 31/07 |
| 93/11755 | 6/1993 | WIPO | A61K 31/07 |
| 93/21146 | 10/1993 | WIPO | C07C 69/76 |
| 94/14777 | 7/1994 | WIPO | C07D 403/20 |
| 95/04036 | 2/1995 | WIPO | C07C 231/54 |
| 96/05165 | 2/1996 | WIPO | C07C 57/50 |

OTHER PUBLICATIONS

Jones, et al., "A dose–response study of 13–cis–retinoic acid in acne vulgaris", *British Jornal of Dermatology*, (1983) 108, 333–343.

Fekrat, et al., "The effect of Oral 13–cis–retinoic Acid on Retinal Redetachment after Surgical Repair in Eyes with Proliferative Vitreoretinopathy", *Ophthalmology*, vol. 102, No. 3 (Mar. 1995), pp. 412–418.

Nagpal, et al., "Separation of Transactivation and AP1 Antagonism Functions of Retinoic Acid Receptor $\alpha^*$", *The Journal of Biological Chemistry*, 270/2(1995): 923–927.

Allegretto, et al., "Transactivation Properties of Retinoic Acid and Retinoid X Receptors in Mammalian Cells and Yeast", *The Journal of Biological Chemistry*, vol 268, No. 35 (Dec. 15, 1993), pp. 26625–26633.

Gruapner, et al., "6'–Substituted Naphthalene–2–Carboxylic Acid Analogs, A New Class of Retinoic Acid Receptor Subtype–Specific Ligands," *Biochemical and Biophysical Research Communications*, vol. 179, No. 3 (Sep. 30, 1991), pp. 1554–1561.

Moore, et al., "Retinoic Acid and Interferon in Human Cancer: Mechanistic and Clinical Studies," *Seminars in Hematology*, 31/4, Suppl 5 (Oct. 1994), pp. 31–37.

"A Convenient Synthesis of Ethynylarenes and Diethynylarenes" by S. Takahashi et al. *Synthesis* (1980) p. 627–630.

Shudo et al. in *Chem. Phar. Bull.*, (1985) 33:404–407.

Kagechika et al. in *J. Med. Chem.*, (1988) 31:2182–2192.

Chemistry and Biology of Synthetic Retinoids by Marcia I. Dawson and William H. Okamura, published by CRC Press Inc., 1990, p. 334–335, 354.

Synthesis of 2,2'–Diacyl–1,1'–Biaryls. Regiocontrolled Protection of . . . by Mervic, et al., *J. Org. Chem.,* (1980) No. 45, p. 4720–4725.

A Dopamine Receptor Model and Its Application in the Design of a New Class of Rigid Pyrrolo[2,3–g]isoquinoline Antipsychotics, Gary L. Olson et al. *American Chemical Societe,* (1981) 24/9:1026–1031.

6.2.3 Conformational Restriction, Williams, et al., *Drug Discovery and Development,* The Humana Press, (1987) pp. 54–55.

V. Retinoid Structure–Biological Activity Relationships, Chemistry and Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid and Acitretin on the Proliferation, Lipid Synthesis and Keratin Expression of Cultured Human Sebocytes in Vitro" C.C. Zouboulis, *The Journal of Investigative Dermatology,* (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology,* (1991) 96/3.

"Synthesis and Evaluation of Stilbene and Dihydrostilbene Derivateives as Potential Anticancer Agents That Inhibit Tubulin Polymerization" by Cushman, Mark et al. *J. Med. Chem.,* (1991), 34:2579–2588.

"Synthesis and Evaluation of New Pretoein Tyrosine Kinase Inhibitors. Part 1. Pyridine–Containing Stilbenes and Amides" by Cushman, Mark et al. *Bioorganic & Medicinal Chemistry Letters,* (1991) 1/4:211–214.

"Di– and Tri–methoxystyryl Derivatives of Heterocyclic Nitrogen Compounds" by Bahner, C. T. et al. *Arzneim–Forsch,/Drug Res,* (1981)31 (I),NR. 3.

"Retinobenzoic acids. 3. Structure–Activity Relationships of Retinoidal Azobenzene–4–Carboxylic Acids and Stilbene–4– Carboxylic Acids" by H. Kagechika et al., *Journal of Medicinal Chemistry,* (1989), 32:1098–1108.

Eyrolles, L. et al. "Retinoid Antagonists: Molecular Design Based on the Ligand Superfamily Concept" *Med. Chem. Res.,* (1992) 2:361–367.

BENZO[1,2-G]-CHROM-3-ENE, AND BENZO [1,2-G]-THIOCHROM-3-ENE DERIVATIVES

CROSS-REFERENCE TO RELATED APPLICATION

The present application is a divisional of application Ser. No. 08/764,466 filed on Dec. 12, 1996, now issued as U.S. Pat. No. 5,728,846.

BACKGROUND OF THE INVENTION

1. Field of the Invention

The present invention relates to novel compounds having retinoid-like, retinoid antagonist and/or retinoid inverse-agonist-like biological activity. More specifically, the present invention relates to aryl or heteroaryl substituted 3,4-dihydroanthracene and aryl or heteroaryl substituted benzo[1,2-g]-chrom-3-ene, benzo[1,2-g]-thiochrom-3-ene and benzo[1,2-g]-1,2-dihydroquinoline derivatives which bind to retinoid receptors and have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil[R,] diseases associated with the immune system, including use of the present compounds as immunosuppressants and immunostimulants, modulation of organ transplant rejection and facilitation of wound healing, including modulation of chelosis.

European Patent Application No. 0 210 929 (published on Feb. 4, 1987) describes polycyclic compounds which are said to have certain retinoid-like, or related biological activity. U.S. Pat. Nos. 4,980,369, 5,006,550, 5,015,658, 5,045, 551, 5,089,509, 5,134,159, 5,162,546, 5,234,926, 5,248,777, 5,264,578, 5,272,156, 5,278,318, 5,324,744, 5,346,895, 5,346,915, 5,348,972, 5,348,975, 5,380,877, 5,399,561 and 5,407,937, (assigned to the same assignee as the present application) and patents and publications cited therein, describe or relate to chroman, thiochroman and 1,2,3,4-tetrahydroquinoline derivatives which have retinoid-like biological activity.

U.S. Pat. Nos. 5,130,335; 5,324,840; 5,344,959; 5,451, 605; 5,455,265; 5,470,999; 5,475,022; 5,475,113; 5,489, 584; 5,514,825; 5,543,534; (assigned to the same assignee as the present application) and patents and publications cited therein, describe or relate to 5,6,7,8-tetrahydronaphthalene or naphthalene derivatives which have retinoid-like biological activity.

Still further, several co-pending applications and recently issued patents which are assigned to the assignee of the present application, are directed to further compounds having retinoid-like activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$, and $RAR_\gamma$, in RXR the subtypes are: $RXR_\alpha$, $RXB_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonist do not effect the receptor equilibrium but are capable of competing for the receptors with both agonists (ligands) and with inverse agonists.

It has been recently discovered and described in pending applications assigned to the same assignee as the present application that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J Med. Chem. 1995, 38, 3163–3173. Kaneko et al. Med. Chem Res. (1991) 1:220–225; Apfel et al. Proc. Natl. Acad. Sci. USA Vol 89 pp 7129–7133 August 1992 Cell Biology; Eckhardt et al. Toxicology Letters, 70 (1994) 299–308; Keidel et al. Molecular and Cellular Biology, Vol 14, No. 1, January 1994, p 287–298; and Eyrolles et al. J. Med. Chem. 1994, 37, 1508–1517 describe compounds which have antagonist like activity at one or more of the RAR retinoid subtypes.

SUMMARY OF THE INVENTION

The present invention relates to compounds of Formula 1

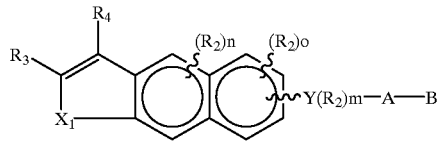

FORMULA 1 wherein $X_1$ is —C($R_1$)$_2$—, —C($R_1$)$_2$—C($R_1$)$_2$—, —S—, —O—, —NR$_1$—, —C($R_1$)$_2$—O—, —C($R_1$)$_2$—S—, or —C($R_1$)$_2$—NR$_1$—;

$R_1$ is independently H or alkyl of 1 to 6 carbons;

$R_2$ is optional and is defined as lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer between 0 and 4;

n is an integer between 0 and 2;

o is an integer between 0 and 3;

$R_3$ is hydrogen, lower alkyl of 1 to 6 carbons, F, Cl, Br or I;

$R_4$ is $(R_5)_p$-phenyl, $(R_5)_p$-naphthyl, or $(R_5)_p$-heteroaryl where the heteroaryl group is 5-membered or 6-membered and has 1 to 3 heteroatoms selected from the group consisting of O, S and N;

p is an integer having the values of 0–5;

$R_5$ is optional and is defined as independently F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl) silyl or (trialkyl)silyloxy group where the alkyl groups independently have 1 to 6 carbons;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is —(CR$_3$═CR$_3$)$_r$—;

r is an integer between 1 and 3;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, with the proviso that when Y is —(CR$_3$═CR$_3$)$_r$— then A is (CH$_2$)$_q$ and q is 0;

B is hydrogen, COOH or a pharmaceutically acceptable salt thereof, $COOR_8$, $CONR_9R_{10}$, —CH$_2$OH, $CH_2OR_{11}$, $CH_2OCOR_{11}$, CHO, CH(OR$_{12}$)$_2$, $CHOR_{13}O$, —COR$_7$, CR$_7$(OR$_{12}$)$_2$, CR$_7$OR$_{13}$O, or Si(C$_{1-6}$alky)$_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assay of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670, 1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\Gamma$ receptors, and the ability or inability of the compounds to activate transcription of a reporter gene through these receptor subtypes can be tested.

Specifically, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 11 2 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A description of the holoreceptor transactivation assay is also provided below.

Holoreceptor Transactivation Assay

CV1 cells (5,000 cells/well) were transfected with an RAR reporter plasmid MTV-TREp-LUC (50 ng) along with one of the RAR expression vectors (10 ng) in an automated 96-well format by the calcium phosphate procedure of Heyman et al. Cell 68, 397–406, (1992). For $RXR_\alpha$ and $RXR_\gamma$ transactivation assays, an RXR-responsive reporter plasmid CRBPII-tk-LUC (50 ng) along with the appropriate RXR expression vectors (10 ng) was used substantially as described by Heyman et al. above, and Allegretto et al. J. Biol. Chem. 268, 26625–26633. For $RXR_\beta$ transactivation assays, an RXR-responsive reporter plasmid CPRE-tk-LUC (50 mg) along with $RXR_\beta$ expression vector (10 mg) was used as described in above. These reporters contain DRI elements from human CRBPII and certain DRI elements from promoter, respectively. (see Mangelsdorf et al. The Retinoids: Biology, Chemistry and Medicine, pp 319–349, Raven Press Ltd., New York and Heyman et al., cited above) (1, 8). A β-galactosidase (50 ng) expression vector was used as an internal control in the transfections to normalize for variations in transfection efficiency. The cells were transfected in triplicate for 6 hours, followed by incubation with retinoids for 36 hours, and the extracts were assayed for luciferase and β-galactosidase activities. The detailed experimental procedure for holoreceptor transactivations has been described in Heyman et al. above, and Allegretto et al. cited above. The results obtained in this assay are expressed in $EC_{50}$ numbers, as they are also in the chimeric receptor transactivation assay. The Heyman et al. Cell 68, 397–406, Allegretto et al. J. Biol. Chem. 268, 26625–26633, and Mangelsdorf et al. The Retinoids: Biology, Chemistry and Medicine, pp 319–349, Raven Press Ltd., New York, are expressly incorporated herein by reference. The results of ligand binding assay are expressed in $K_d$ numbers. (See Cheng et al. Biochemical Pharmacology Vol. 22 pp 3099–3108, expressly incorporated herein by reference.)

Table 1 shows the results of the ligand binding assay for certain exemplary compounds of the invention for the receptor subtypes in the RAR group.

TABLE 1

Ligand Binding Assay

| Compound No. | $K_d$ (nanomolar, nM) | | |
|---|---|---|---|
| | RARα | RARβ | RARγ |
| 2 | 13 | 4 | 7 |
| 4 | 15 | 6 | 11 |
| 12 | 17 | 12 | 33 |

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference.

In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. EMBO J. 12, 2349–2360 (1933) expressly incorporated herein by reference. Retinoid inverse agonists are able to inhibit the basal luciferase activity in these cells in a dose dependent manner and $IC_{50}$s measured. In this assay, Compound 2 had an $IC_{50}$ of 1.0 nM.

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alky, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well. In the present application when no specific mention is made of the configuration (cis, trans, or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended.

The numbering system used in the naming of the compounds of the present invention, as well as of the intermediate compounds utilized in the synthetic routes leading to the compounds of the invention, is illustrated below for 3,4-dihydroanthracene, benzo[1,2-g]-chrom-3-ene, benzo[1,2-g]-thiochrom-3-ene and benzo[1,2-g]-1,2-dihydroquinoline and for 3,4-dihydro-4,4-dimethyl-7-bromo-1(2H)-naphthalenone.

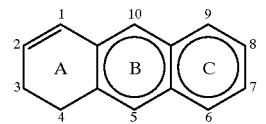
3,4-dihydroanthracene

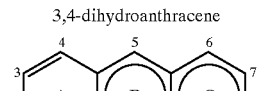
benzo[1,2-g]-chrom-3-en

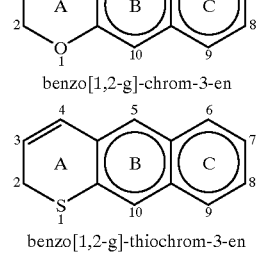
benzo[1,2-g]-thiochrom-3-en

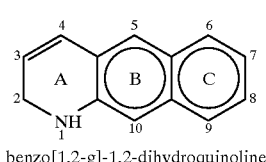
benzo[1,2-g]-1,2-dihydroquinoline

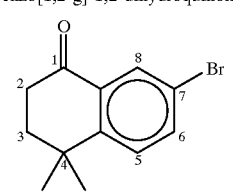
3,4-dihydro-4,4-dimethyl-7-bromo-1(2H)-naphthalenone

Generally speaking, the 3,4-dihydroanthracene compounds of the invention are prepared in synthetic steps which usually first involve the multistep preparation of a 3,4-dihydronaphthalene derivative that already includes the desired $R_1$, $R_2$, $R_3$ and $R_4$ substituents and an aldehyde function in the 6 or 7-position of the 3,4-dihydronaphthalene nucleus. For the preparation of benzo[1,2-g]-chrom-3-ene, benzo[1,2-g]-thiochrom-3-ene and benzo[1,2-g]-1,2-dihydroquinoline derivatives of the invention, the first (usually multi-step) procedure involves the preparation of a chrom-3-ene, thiochrom-3-ene or 1,2-dihydroquinoline derivative which already includes the desired $R_1$, $R_2$, $R_3$ and $R_4$ substituents of the compounds of the invention, and an aldehyde function in the 6 or 7-position of the chrom-3-ene, thiochrom-3-ene or 1,2-dihydroquinoline nucleus. The aldehyde is then reacted in a Horner Emmons or Wittig, or like reaction with an aryl or heteroaryl phosphonate that carries a side chain capable of cyclizing with the carbocyclic aromatic group of the 3,4-dihydronaphthalene, chrom-3-ene, thiochrom-3-ene or 1,2-dihydroquinoline intermediate. The latter cyclization reaction forms the "C" ring of the 3,4-dihydroanthracene, benzo[1,2-g]-chrom-3-ene, benzo[1,2-g]-thiochrom-3-ene and benzo[1,2-g]-1,2-dihydroquinoline compounds of the invention.

Details of the above-outlined generalized synthetic schemes are provided below in connection with the description of the specific embodiments and specific examples.

The synthetic methodology employed for the synthesis of the compounds of the present invention may also include transformations of the group designated —A—B in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

To increase the value of q in the compounds of the invention (or precursors thereof) before affecting the coupling or linkage in a Horner Emmons or like reaction with the aldehyde on the 3,4-dihydronaphthalene, chrom-3-ene, thiochrom-3-ene or 1,2-dihydroquinoline nucleus (where such compounds are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph and converted into phosphonates of phosphonium salts suitable for the Horner Emmons or Wittig reaction. Compounds of the invention as set forth in Formula 1 (or precursors thereof) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of the invention or precursors thereof, where the A group has a triple (acetylenic) bond, can be made by reaction of a corresponding aromatic methyl ketone with strong base, such as lithium diisopropylamide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from the corresponding halogenated aromatic or heteroaromatic compounds, preferably where the halogen is I.

SPECIFIC EMBODIMENTS

With reference to the symbol Y in Formula 1, the preferred compounds of the invention are those where Y is phenyl, naphthyl, pyridyl, thienyl or furyl. Even more preferred are compounds where Y is phenyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no $R_2$ substituent on the Y group.

The A—B group of the preferred compounds is $(CH_2)_q COOH$ or $(CH_2)_q$—$COOR_8$, where $R_8$ is defined as above. Even more preferably q is zero and $R_8$ is lower alkyl.

The aromatic carbocyclic portions (B and C rings) of the 3,4-dihydroanthracene moiety, or of the benzo[1,2-g]-chrom-3-ene, benzo[1,2-g]-thiochrom-3-ene and benzo[1,2-g]-1,2-dihydroquinoline moiety of the compounds of the invention (as applicable) are preferably substituted only by the —Y$(R_2)_m$—A—B group. In other words, in the preferred compounds there is no $R_2$ substituent (other than hydrogen) on the aromatic carbocyclic portion of the condensed ring system. Similarly, in the preferred compounds of the invention there is no $R_3$ substituent (other than hydrogen).

The moiety designated $X_1$ in Formula 1 is preferably —$C(R_1)_2$—$C(R_1)_2$—, —$C(R_1)_2$—O—, —$C(R_1)_2$—S—, or —$C(R_1)_2$—$NR_1$—, and $R_1$ is preferably H or methyl. The —Y$(R_2)_m$—A—B group is preferably attached to the 8-position of the 3,4-dihydroanthracene nucleus and to the 7-position of the benzo[1,2-g]-chrom-3-ene, benzo[1,2-g]-thiochrom-3-ene and benzo[1,2-g]-1,2-dihydroquinoline nucleus, as applicable.

Referring now to the $R_4$ substituent in the compounds of Formula 1 compounds are preferred where this substituent is phenyl, $R_5$-substituted phenyl, pyridyl, $R_5$-substituted pyridyl, thienyl, or $R_5$-substituted thienyl. Even more preferred are compounds where the $R_4$ substituent is phenyl, 4-methylphenyl, 3-pyridyl and particularly 6-methyl-3-pyridyl, 2-thienyl and particularly 5-methyl-2-thienyl.

The most preferred compounds of the invention are listed below in Table 2 with reference to Formula 2 or Formula 3, as applicable.

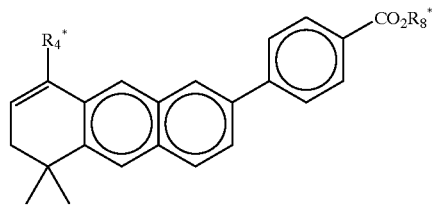

Formula 2

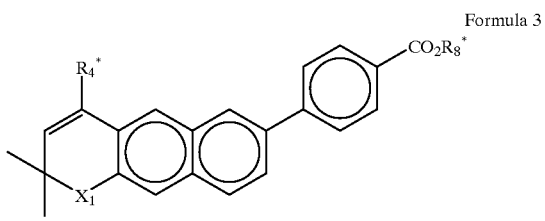

Formula 3

TABLE 2

| Compound No. | Formula | $X_1$* | $R_4$* | $R_8$* |
|---|---|---|---|---|
| 1 | 2 | — | 4-methylphenyl | Et |
| 2 | 2 | — | 4-methylphenyl | H |
| 3 | 2 | — | 5-methyl(2-thienyl) | Et |
| 4 | 2 | — | 5-methyl(2-thienyl) | H |
| 5 | 2 | — | 6-methyl(3-pyridyl) | Et |
| 6 | 2 | — | 6-methyl(3-pyridyl) | H |
| 7 | 3 | S | 4-methylphenyl | Et |
| 8 | 3 | S | 4-methylphenyl | H |
| 9 | 3 | O | 4-methylphenyl | Et |

TABLE 2-continued

| Compound No. | Formula | $X_1$* | $R_4$* | $R_8$* |
|---|---|---|---|---|
| 10 | 3 | O | 4-methylphenyl | H |
| 11 | 3 | O | 5-methyl(2-thienyl) | Et |
| 12 | 3 | O | 5-methyl(2-thienyl) | H |
| 13 | 3 | S | 5-methyl(2-thienyl) | Et |
| 14 | 3 | S | 5-methyl(2-thienyl) | H |

The compounds of this invention can be made by the general procedures outlined above under the title ""GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formula 1.

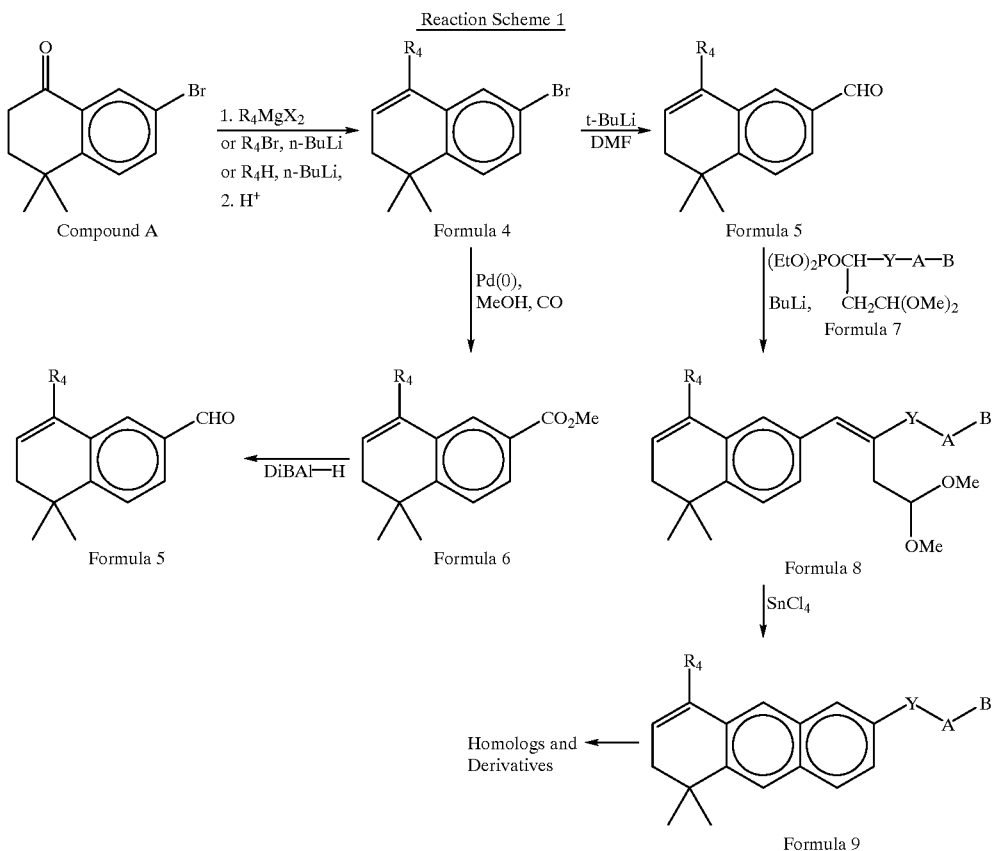

Reaction Scheme 1

Referring now to Reaction Scheme 1 a synthetic process is described whereby compounds of the invention are obtained in which, with reference to Formula 1, $X_1$ is —$C(R_1)_2$—$C(R_1)_2$— and the Y group is phenyl, naphthyl or heteroaryl. In other words Reaction Scheme 1 describes an example of a synthetic route for preparing compounds of the invention which are 3,4-dihydroanthracene derivatives. The reaction scheme discloses this synthetic route for the preferred examples in which the Y group is coupled to the 8 position of the 3,4-dihydroanthracene nucleus, and the 4-position bears two (geminal) methyl substituents. Nevertheless, those skilled in the art will readily understand that the synthetic steps of Reaction Scheme 1 can be readily modified, within the skill of the art, to yield other 3,4-dihydroanthracene compounds of the invention. The starting materials for the synthetic route of Reaction Scheme 1 are 6 or 7-bromo (or like halogeno) substituted 1-(2H)-naphthalenones. Specifically, for the examplary synthetic route illustrated in Reaction Scheme 1 the starting material is 3,4-dihydro-4,4-dimethyl-7-bromo-1(2H)-naphthalenone (Compound A). Compound A can be obtained in accordance with the chemical scientific (Johnson et al. , J. Med. Chem. 1995, 38, 4764–4767) and patent (U.S. Pat. No. 5,543,534) literature. The Johnson et al. publication and the specification of U.S. Pat. No. 5,543,534 are expressly incorporated herein by reference. Another example for the starting material in Reaction Scheme 1 is 3,4-dihydro-4,4-dimethyl-6-bromo-1(2H)-naphthalenone. The latter compound, when subjected to the reactions disclosed in this scheme, gives rise to 3,4-dihydroanthracene compounds of the invention where the Y group is coupled to the 7-position of the 3,4-dihydroanthracene nucleus. 3,4-Dihydro-4,4-dimethyl-6-bromo-1(2H)-naphthalenone can also be obtained in accordance with the chemical scientific (Mathur et al. Tetrahedron, 41, 1509 1516 (1985)) and patent (U.S. Pat. No. 5,543,534) literature.

In accordance with Reaction Scheme 1, 3,4-dihydro-4,4-dimethyl-7-bromo-1(2H)-naphthalenone (Compound A) is reacted with a Grignard reagent of the formula $R_4$—Mg—$X_2$, where $R_4$ is an aryl or heteroaryl group as defined in connection with Formula 1, and $X_2$ is halogen, preferably bromine. The product of the Grignard (or analogous) reaction is a tertiary alcohol (not shown in the reaction scheme) which is dehydrated by treatment with acid, to give a 1-aryl or 1-heteroaryl-7-bromo-3,4-dihydronaphthalene derivative of Formula 4. An example for a Grignard reagent used in the synthesis of preferred compounds of the invention is the reagent obtained from 4-bromotoluene with magnesium. An alternative method for obtaining the 1-aryl or 1-heteroaryl-7-bromo-3,4-dihydronaphthalene derivatives of Formula 4 is a reaction between an aryl or heteroaryl halide of the formula $R_4$—$X_2$ ($R_4$ and $X_2$ are defined as above, $X_2$ is preferably Br) with Compound A in the presence of strong base, such as n-butyl lithium. A suitable reagent for this reaction is, for example, 2-methyl-5-bromopyridine. As still another alternative, Compound A is reacted with the lithium (or other suitable metal) salt of the formula $R_4$—Li, ($R_4$ is defined as above), that can be obtained by reaction between a heteroaryl compound (such as 2-methylthiophene) and n-butyl lithium.

In the next step of the reaction sequence disclosed in Reaction Scheme 1, the 1-aryl or 1-heteroaryl-7-bromo-3,4-dihydronaphthalene derivatives of Formula 4 are reacted with dimethylformamide (DMF) in the presence of tertiary-butyl lithium to provide the 1-aryl or 1-heteroaryl-3,4-dihydronaphthalene-7-aldehydes of Formula 5. The aldehyde compounds of Formula 5 can also be obtained by first converting the 7-bromo function of the compounds of Formula 4 into a carboxylic acid ester function or carboxylic acid, to give the 1-aryl or 1-heteroaryl-3,4-dihydronaphthalene-7-carboxylic acid esters (or acids, not shown in the scheme) of Formula 6. The carboxylic acid methyl ester derivative is obtained, for example by reaction with carbon monoxide and methanol in the presence of palladium[2]bis(triphenylphoshine)chloride and 1,3-bis (diphenylphosphino)propane, as shown in the scheme. The compounds of Formula 6 are reduced with a suitable reducing agent, such as diisobutyl aluminum hydride (DiBAl—H) to provide the 1-aryl or 1-heteroaryl-3,4-dihydronaphthalene-7-aldehydes of Formula 5.

The aldehydes of Formula 5 are subjected to a Horner Emmons type reaction, in the presence of strong base such as n-butyl lithium in hexane, with a 1-aryl or 1-heteroaryl 1-diethoxyphosphoryl-3,3-dimethoxypropane derivative of Formula 7. An example of the phosphonate compound, which is used in the preparation of several preferred compounds of the invention, is ethyl 4-(diethoxyphosphoryl-3,3-dimethoxypropyl)benzoate. Ethyl 4-(diethoxyphosphoryl-3,3-dimethoxypropyl)benzoate is available in accordance with the procedure of EPO Application No. 0 210 929 (published on Feb. 4, 1987, Shroot et al.) which is incorporated herein by reference. In accordance with the Shroot et al. reference the reagent ethyl 4-(diethoxyphosphoryl-3,3-dimethoxypropyl)benzoate is made starting with ethyl 4-bromobenzoate that is reacted with dimetyl acetal of acryl aldehyde, the product is hydrogenated and subsequently brominated (with N-bromo succinimide) and thereafter reacted with triethylphosphite.

Other examples for the phoshonates of Formula 7 are ethyl 2-(diethoxyphosphoryl- 3,3-dimethoxypropyl) pyridine-5-carboxylate, ethyl 2-(diethoxyphosphoryl-3,3-dimethoxypropyl)pyridine-6-carboxylate, ethyl 2-(diethoxyphosphoryl-3,3-dimethoxypropyl)thiophene-4-carboxylate, ethyl 2-(diethoxyphosphoryl-3,3-dimethoxypropyl)thiophene-5-carboxylate, ethyl 2-(diethoxyphosphoryl-3,3-dimethoxypropyl)furan-4-carboxylate, ethyl 2-(diethoxyphosphoryl-3,3-dimethoxypropyl)furan-5-carboxylate. These and analogous phosphonate reagents within the scope of Formula 7 can be obtained by appropriate modification of the procedure described in the Shroot et al. reference.

The product of the Horner Emmons reaction between the 1-aryl or 1-heteroaryl-3,4-dihydronaphthalene-7-aldehydes of Formula 5 and the 1-aryl or 1-heteroaryl 1-diethoxyphosphoryl-3,3-dimethoxypropane derivative of Formula 7 is a disubstituted ethene compound of Formula 8. Those skilled in the art will readily understand that instead of a Horner Emmons reaction, a Wittig reaction can also be employed, utilizing the appropriate phosphonium derivative, to provide compounds of Formula 8.

The disubstituted ethene compounds of Formula 8 are cyclized, for example by heating in a neutral solvent (such as dischloromethane), in the presence of $SnCl_4$ or other suitable Friedel Crafts type catalyst, to form the "C ring" of the 3,4-dihydroanthracene derivatives of the invention, within the scope of Formula 9. The compounds of Formula 9 can be converted into further compounds of the invention by reaction well known to the synthetic organic chemist, such as saponification, esterification, amide formation and homologation. These reactions were briefly described above, and the syntheses of these further compounds of the invention is indicated in Reaction Scheme 1 as conversion to "HOMOLOGS AND DERIVATIVES'.

REACTION SCHEME 2

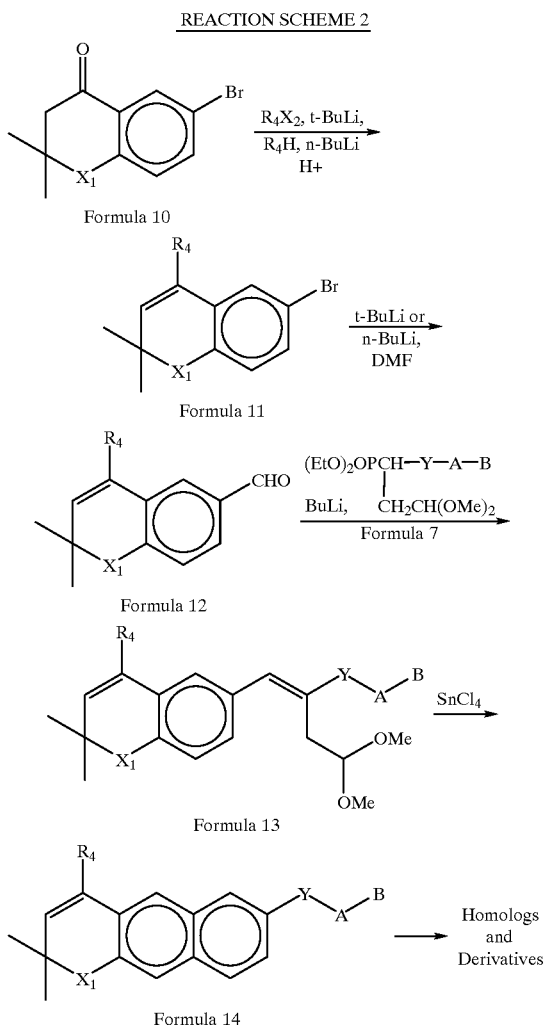

Reaction Scheme 2 discloses the synthesis of compounds of the invention where with reference to Formula 1 the $X_1$ group is —$C(R_1)_2$—O—, —$C(R_1)_2$—S—, or —$C(R_1)_2$—$NR_1$— where the Y group is phenyl, naphthyl or heteroaryl and the $R_1$ group is defined as in connection with Formula 1. In other words, Reaction Scheme 2 discloses the preferred synthetic routes to compounds of the invention which are benzo[1,2-g]-chrom-3-ene, benzo[1,2-g]-thiochrom-3-ene and benzo[1,2-g]-1,2-dihydroquinoline derivatives. As in Reaction Scheme 1 in this scheme also the description is directed to a synthetic route for the preferred examples in which the Y group is coupled to the 8 position of the tricyclic condensed ring. In these preferred examples the 2-position of the tricyclic condensed ring bears two (geminal) methyl substituents. Nevertheless, those skilled in the art will readily understand that the synthetic steps of Reaction Scheme 2 can be readily modified, within the skill of the art, to yield other benzo[1,2-g]-chrom-3-ene, benzo[1,2-g]-thiochrom-3-ene and benzo[1,2-g]-1,2-dihydroquinoline compounds of the invention.

6-Bromochroman-4-one, 6-bromothiochroman-4-one and 6-bromo-1,2,3,4-tetrahydroquinoline-4-one derivatives of Formula 10 serve as starting materials in the steps shown in Reaction Scheme 1. Specifically, 2,2-dimethyl-6-bromo-thiochroman-4-one can be obtained from the reaction of thiophenol with 3,3-dimethylacrilic acid, followed by cyclization of the resulting adduct, as is described in detail in the "Specific Examples" section of this application. 2,2-Dimethyl-6-bromochroman-4-one can be obtained in accordance with the procedure of Buckle et al. J. Med. Chem. 1990 33, 3028, which is expressly incorporated herein by reference. 2,2-Dimethyl-6-bromo-1,2,3,4-tetrahydroquinoline can be obtained by bromination with N-bromosuccinimide of 2,2-dimethyl-1,2,3,4-tetrahydroquinoline that is available in accordance with the chemical literature (Helv. Chim. Acta (1990) 73, 1515–1573).

In accordance with Reaction Scheme 2, the 6-bromochroman-4-one, 6-bromothiochroman-4-one or 6-bromo-1,2,3,4-tetrahydroquinoline-4-one derivative of Formula 10 is reacted with a reagent of the formula $R_{4X2}$, where $X_2$ is halogen, preferably bromine, in the presence of strong base, such as tertiary-butyl lithium or normal-butyl lithium. $R_4$ and $X_2$ are defined as in connection with Reaction Scheme 1. 4-aryl or 4-heteroaryl 6-bromochrom-3-ene, 4-aryl or 4-heteroaryl 6-bromothiochrom-3-ene or 4-aryl or 4-heteroaryl 6-bromo-1,2,dihydroquinoline derivatives of Formula 11 are obtained in this reaction after acid catalyzed dehydration of the tertiary alcohol intermediate that is first formed in the reaction with $R_4$—$X_2$. A Grignard reagent of the formula $R_4$—Mg—$X_2$, or the metal salt, particularly the lithium salt, of an aryl or heteroaryl compond of the forula $R_4$—Li can also be employed, to yield the 4-aryl or 4-heteroaryl derivatives of Formula 11. The 4-aryl or 4-heteroaryl 6-bromochrom-3-ene, 4-aryl or 4-heteroaryl 6-bromothiochrom-3-ene or 4-aryl or 4-heteroaryl 6-bromo-1,2,dihydroquinoline derivatives of Formula 11 are converted into the aryl or heteroaryl substituted benzo[1,2-g]-chrom-3-ene, benzo[1,2-gl-]-thiochrom-3-ene and benzo[1,2-g]-1,2-dihydroquinoline compounds of the invention in the same, or substantially the same sequence of reactions, as is described in Reaction Scheme 1. This sequence of reactions is shown in Reaction Scheme 2, and specific examples for their application are described in the "Specific Examples" section. The disubstituted ethene compounds of Formula 13 are usually not isolated in a pure form. Rather they are subjected to a cyclization reaction without purification to provide the compounds of Formula 14, which can be further converted into homologs and derivatives still within the scope of the invention.

Compounds of the invention where with reference to Formula 1 the $X_1$ group is —$C(R_1)_2$— can be made in analogy to the synthetic steps outlined in Reaction Scheme 1, starting with 6-bromo-indan-1-one or from an appropriately subtituted derivative. In these synthetic schemes 6-bromo-indan-1-one is used in analogy to 7-bromo-3,4-dihydro-4,4-dimethylnaphthalen-1(2H)-one (Compound A) as a starting material. 6-bromo-3,3-dimethyl-indan-1-one is available accordance with the chemical literature. (See Smith et al. Org. Prep. Proced. Int., 1978, 10 123–131.)

Compounds of the invention where with reference to Formula 1, $X_1$ is O, S, or $NR_1$ can be made from the compounds 5-bromo-benzofuran-3-(2H)-one, 5-bromo-benzothiophene-3-(2H)-one and 5-bromo-indol-3-(2H)-one, or from their appropriately substituted derivatives, substantially in accordance with the reaction steps set forth in Reaction Scheme 1. These are available in accordance with the chemical literature. For 5-bromo-benzofuran-3(2H)-one see Ellingboe et al. J. Med. Chem. (1992) 35 p1176, and for 5-bromo-benzothiophene-3-(2H)-one see Pummerel et al. Chem. Ber. 42 (1909) 2279. 5-Bromo-indol-3-(2H) one can be obtained from 5-bromo-indol-2,3-dione (Patrick et al.

Tet. Letts. (1984) 25 3099) by reduction with LiAlH$_4$, followed by oxidation with manganese dioxide (MnO$_2$).

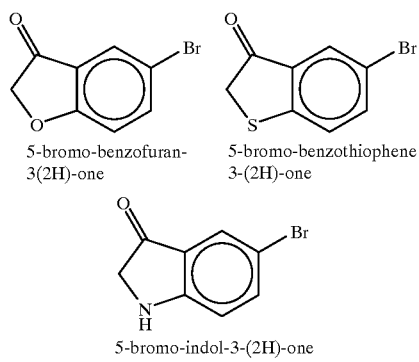

5-bromo-benzofuran-3(2H)-one 5-bromo-benzothiophene 3-(2H)-one 5-bromo-indol-3-(2H)-one Reaction Scheme 3 provides an example for the preparation of compounds of the invention where with reference to Formula 1 Y is —(CR$_3$=CR$_3$)$_r$— and r is 2, although those skilled in the art will be able to readily modify the steps depicted in this reaction scheme to obtain additional compounds of the invention where r is 1 or 3. The dimethyl acetal of ethyl 4-oxobutyrate is the starting material in accordance with this scheme. The latter compound can be obtained in accordance with the publication Smith et al. J. Am. Chem. Soc. 113 (6) 1991 pp 2071–2073. The dimethyl acetal of ethyl 4-oxobutyrate is brominated with N-bromosuccinimide, and the resulting dimethyl acetal of 2-bromo-4-oxobutyrate is reacted with triethylphosphite to give the dimethyl acetal of ethyl 2-diethylphosphoryl-2-oxo-butyrate. The dimethyl acetal of ethyl 2-diethylphosphoryl-2-oxo-butyrate is reacted in a Horner Emmons type reaction, in the presence of strong base such as n-butyl lithium, with an aldehyde of Formula 15. In Formula 15 R$_4$ and X$_1$ are defined as in connection with Formula 1. Therefore, the

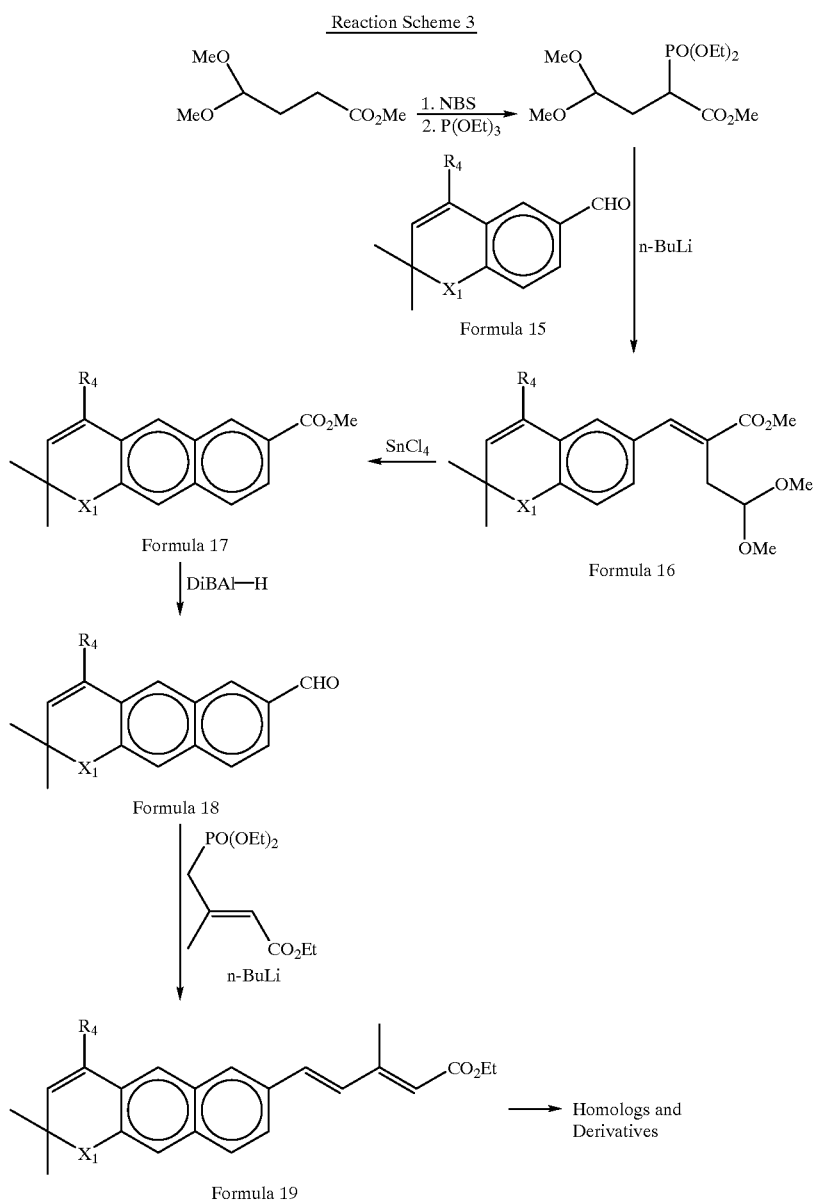

Reaction Scheme 3 aldehyde of Formula 15 can be an aldehyde derivative of 1-aryl or 1-heteroaryl 1,2,3,4-tetrahydronaphthalene or of a 4-aryl or 4-heteroaryl chrom-3-ene, 4-aryl, 4-heteroaryl thiochrom-3-ene, or 4-aryl or 4-heteroaryl 1,2-dihydroquinoline. More specific examples for the aldehydes which are used in this reaction scheme are the aldehydes of Formula 5 disclosed in connection with Reaction Scheme 1, and the aldehydes of Formula 12 disclosed in connection with Reaction Scheme 2. The product of the Horner Emmons condensation reaction is a pentenoic acid derivative of Formula 16, which is cyclized in the subsequent reaction step to provide an ethyl carboxylate derivative of the aryl or heteroaryl substituted 3,4-dihydroanthracene or aryl or heteroaryl substituted benzo[1,2-g]-chrom-3-ene, benzo[1,2-g]-thiochrom-3-ene and benzo[1,2-g]-1,2-dihydroquinoline compounds shown in Formula 17. The ethyl carboxylate function of the compounds of Formula 17 is reduced with a suitable reducing agent, such as diisobutyl aluminum hydride (DiBAl—H), to provide the aryl or heteroaryl substituted 3,4-dihydroanthracene aldehyde, aryl or heteroaryl substituted benzo[1,2-g]-chrom-3-ene aldehyde, benzo[1,2-g]-thiochrom-3-ene and benzo[1,2-g]-1,2-dihydroquinoline aldehyde compounds of Formula 18. The aldehydes of Formula 18 are then reacted in another Horner Emmons reaction with ethyl-diethylphosphono-3-methyl 2(E)butenoate which can be obtained in acordance with the literature procedure of Corey et al. J. Org. Chem. (1974) 39 p821. The product of this last Horner Emmons reaction is the pentadienoic acid derivative of Formula 19 which is within the scope of the present invention. The compounds of Formula 19 can be converted into further homologs and derivatives still within the scope of the invention, as described above.

4-heteroaryl chrom-3-ene, 4-aryl, 4-heteroaryl thiochrom-3-ene, or 4-aryl or 4-heteroaryl 1,2-dihydroquinoline compound of Formula 15 is reacted with the Wittig reagent [2-(1,3-dioxolan-2-yl)ethyl)-triphenylphosphonium bromide in the presence of strong base, such as n-butyl lithium. Specific examples for the aldehydes which are used in this reaction scheme are the aldehydes of Formula 5 disclosed in connection with Reaction Scheme 1, and the aldehydes of Formula 12 disclosed in connection with Reaction Scheme 2. The Wittig reagent [2-(1,3-dioxolan-2-yl)ethyl) triphenylphosphonium bromide is commercially available from Aldrich Chemical Company Inc. The product of the Wittig reaction is a disubstituted ethene compound of Formula 20. The aryl or heteroaryl substituent designated "Y" is introduced into this molecule in a Heck reaction, utilizing a halogen substituted aryl or heteroaryl compound of the formula $X_2$—Y—A—B where $X_2$ is halogen, preferably bromine or iodine, A and B are defined as in connection with Formula 1, and Y is aryl or heteroaryl as defined in Formula 1. Examples for the reagents of formula $X_2$—Y—A—B are ethyl 4-bromobenzoate, ethyl 2-bromopyridine-5-carboxylate, ethyl 2-bromopyridine-6-carboxylate, ethyl 2-bromothiophene-4-carboxylate, ethyl 2-bromothiophene-5-carboxylate, ethyl 2-bromofuran-4-carboxylate, and ethyl 2-bromofuran-5-carboxylate. The Heck reaction is well known in the art, and is usually conducted in a basic solvent, such as triethylamine, in the presence of a phosphine catalyst (such as tris(2-methylphenyl)phosphine or tri-O-tolylphosphine) and in the presence of palladium(II)acetate catalyst. The product of the Heck reaction is a disubstituted ethene compound of Formula 21 which is thereafter ring closed under Friedel Crafts like conditions (e. g. in the presence of $SnCl_4$) as in the analogous reactions described

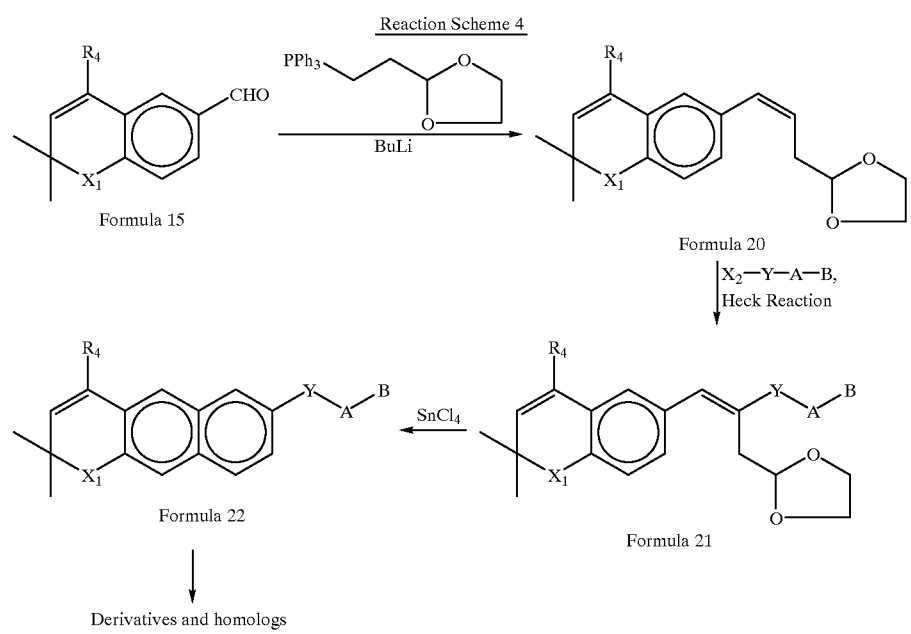

Reaction Scheme 4

Reaction Scheme 4 discloses an alternative synthetic route for preparing the compounds of the invention where, with reference to Formula 1, the Y group is aryl or heteroaryl, as specifically defined in connection with that formula. In accordance with this scheme, the aldehyde derivative of a 1-aryl or 1-heteroaryl 1,2,3,4-tetrahydronaphthalene compound or of a 4-aryl or in Reaction Schemes 1 and 2, to provide the compounds of Formula 22. The compounds of Formula 22 are within the scope of the invention, and can be converted into further compounds of the invention by reactions well known in the art. This is designated symbolically in the reaction scheme by showing conversion into homologs and derivatives.

SPECIFIC EXAMPLES

1-(Tol-4-yl)3,4-dihydro-4,4-dimethyl-7-bromo-naphthalene (Compound B)

To a mixture of Mg metal (650 mg, 27 mmol) in THF (20 mL) was added 4-bromotoluene (5.3 g, 31 mmol) in THF (40 mL). The mixture was stirred for 2 hours at ambient temperature and heated to 70° C. for 30 minutes. After cooling to ambient temperature, 3,4-dihydro-4,4-dimethyl-7-bromo-1(2H)-naphthalenone (Compound A) (2.1 g, 8 mmol), in THF (5 mL) was added and heated to 70° C. for 24 hours. The mixture was cooled to ambient temperature and the reaction was quenched by addition of $H_2O$. The mixture was diluted with ether:ethylacetate (1:1, 100 mL) and washed with saturated $NH_4Cl$ (15 mL), water (10 mL) and brine (10 mL). The organic layer was dried with $MgSO_4$. Solvent was removed under reduced pressure to afford the crude product as an oil. The product was dissolved in THF (20 mL). To this solution p-toleune sulfonic acid (pTSA) (35 mg) was added and the mixture was refluxed for 16 hours. The mixture was cooled to ambient temperature, diluted with ethylacetate (160 mL), washed with 10% $NaHCO_3$ (20 mL), brine (20 mL), dried with $MgSO_4$ and the solvent was removed by evaporation. Purification by chromatography on silica gel gave the title compound as a white solid.

$^1$HNMR ($CDCl_3$): δ1.33 (s, 6H), 2.34 (d, J=4.8 Hz, 2H), 2.42 (s, 3H), 6.00 (t, J=4.8 Hz, 1H), 7.17 (d, J=2.1 Hz, 1H), 7.20–7.30 (m, 5H), 7.34 (dd, J=2.1, 8.2 Hz, 1H).

1-(Tol-4-yl)3,4-dihydro-4,4-dimethyl-7-naphthaldehyde (Compound C)

To a cold (−78° C.), stirred solution of 1-(tol-4-yl)3,4-dihydro-4,4-dimethyl-7-bromo-naphthalene (Compound B 1 g, 3.2 mmol), in THF (17 mL) was added t-BuLi in pentane (1.7M solution, 3 mL, 5.1 mmol). After 10 minutes dry dimethylformamide (DMF) (600 mg, 8 mmol) was added and the dry-ice cooling was replaced with ice-water bath. The mixture was gradually warmed to ambient temperature and diluted with ethylacetate (150 mL), washed with water (15 mL). The organic layer was dried with $MgSO_4$ and solvent was removed under reduced pressure. The crude material was purified by silicagel chromatography to afford the title compound as a white solid.

$^1$HNMR ($CDCl_3$): δ1.38 (s, 6H), 2.39 (d, J=4.9 Hz, 2H), 2.43 (s, 3H), 6.06 (t, J=4.9 Hz, 1H), 7.20–7.30 (m, 4H), 7.50–7.60 (m, 2H), 7.76 (dd, J=1.8, 8.0 Hz, 1H), 9.87 (s, 1H).

Ethyl 4-[1-(2,2-dimethoxyethyl)-2-{1(tol-4-yl)3,4-dihydro-4,4-dimethyl-naphthalen-7-yl}-(E)-ethenyl]-benzoate (Compound E)

To a cold (−78° C.) solution of ethyl 4-(diethoxyphosphoryl-3,3-dimethoxypropyl)benzoate (Compound D, 350 mg, 0.9 mmol, available in accordance with EPO Application No. 0 210 929 published on Feb. 4, 1987), in THF (9 mL), was added n-BuLi in hexane (1.6M solution, 0.7 mL, 1.1 mmol). The mixture was stirred for 1.5 hours. To this solution 1-(tol-4-yl)3,4-dihydro-4,4-dimethyl-7-naphthaldehyde (Compound C, 200 mg, 0.72 mmol), in THF (1 mL) was added and the mixture was gradually warmed to ambient temperature (4 h). The reaction was quenched by adding water (5 mL), and extracted with ethyl acetate (3×25 mL). The organic layer was washed with brine (10 mL), dried with $MgSO_4$ and the solvent was removed by distillation. The crude material was purified by silicagel chromatography to afford the title compound as a colorless oil.

$^1$HNMR ($CDCl_3$): δ1.37 (s, 6H), 1.11 (t, J=7.1 Hz, 3H), 2.35 (d, J=4.6 Hz, 2H), 2.39 (s, 3H), 3.03 (d, J=5.9 Hz, 2H), 3.13 (s, 6H), 4.29 (t, J=5.9 Hz, 1H), 4.39 (q, J=7.1 Hz, 2H), 5.98 (t, J=4.6 Hz, 1H), 6.73 (s, 1H), 7.13 (s, 1H), 7.20 (d, J=8.2 Hz, 2H), 7.27 (d, J=8.2 Hz, 2H), 7.40 (brs, 2H), 7.48 (d, J=8.3 Hz, 2H), 8.02 (d, J=8.3 Hz, 2H).

Ethyl 4 [1(tol-4-yl)-3,4-dihydro-4,4-dimethyl-anthracen-8-yl]-benzoate (Compound 1)

To a cold (−50° C.) solution of ethyl 4-[1-(2,2-dimethoxyethyl)-2-{1(tol-4-yl)3,4-dihydro-4,4-dimethyl-naphthalen-7-yl}-(E)-ethenyl]-benzoate (Compound E, 19 mg, 0.04 mmol), in dichloromethane (3 mL), was added $SnCl_4$ (2 mg in 0.1 mL of dichloromethane). After 15 minutes the reaction was quenched by adding water (2 mL), extracted with ether (60 mL). The organic layer was washed with water (5 mL), brine (5 mL), dried with $MgSO_4$ and the solvent was removed by distillation. The product was purified by silicagel chromatography to afford the title compound as a white solid.

$^1$HNMR ($CDCl_3$): δ1.43 (t, J=7.1 Hz, 3H), 1.47 (s, 6H), 2.42 (d, J=4.9 Hz, 2H), 2.45 (s, 3H), 4.41 (q, J=7.1 Hz, 2H), 6.08 (t, J=4.9 Hz, 1H), 7.25 (d, J=8.0 Hz, 2H), 7.34 d, J=8.0 Hz, 2H), 7.54 (s, 1H), 7.69 (dd, J=1.9, 8.4 Hz, 1H), 7.73 (d, J=8.4 Hz, 2H), 7.79 (s, 1H), 7.87 (d, J=8.4 Hz, 1H), 7.90 (brs, 1H), 8.11 (d, J=8.4 Hz, 2H).

4-[1(Tol4-yl)-3,4-dihydro-4,4-dimethyl-anthracen-8-yl]-benzoic acid (Compound 2)

To a degassed solution of ethyl 4-[1(tol-4-yl)3,4-dihydro-4,4-dimethyl-anthracen-8-yl]-benzoate (Compound 1, 35 mg, 0.08 mmol), in THF (1.5 mL) and MeOH (1.5 mL) was added LiOH (1M solution in water, 0.3 mL, 0.3 mmol). The mixture was stirred at ambient temperature for 16 hours, diluted with ether (60 mL). The mixture was acidified with 10% HCl to pH 4, the product was isolated as an ether insoluble white solid.

$^1$HNMR (DMSO-$D_6$): δ1.11 (s, 6H), 2.38 (s, 3H), 2.39 (d, J=4.5 Hz, 2H), 6.07 (t, J=4.5 Hz, 1H), 7.25–7.33 (m, 4H), 7.51 (s, 1H), 7.84 (dd, J=1.6, 8.6 Hz, 1H), 7.90–8.05 (m, 6H), 8.15 (s, 1H).

1-(5-Methyl-thien-2-yl)3,4-dihydro-4,4-dimethyl-7-bromo-naphthalene (Compound F)

To a cold (−78° C.) solution of 2-methylthiophene (800 mg, 8.1 mmol) in THF (10 mL) was added n-BuLi (1.6M solution in hexane, 5 mL). The mixture was stirred for 1.5 hours and transferred to a cold (−78° C.) flask containing 3,4-dihydro-4,4-dimethyl-7-bromo-1(2H)-naphthalenone (Compound A, 1.63 g, 6.5 mmol), in THF (15 mL). The mixture was gradually warmed to 0° C. The reaction mixture was diluted with ether:ethylacetate (1:1, 80 mL), washed with water (10 mL), brine (10 mL), dried with $MgSO_4$ and the solvent was removed by evaporation. The crude material was dissolved in dichloroethane (20 mL) and pTSA (40 mg) was added. The mixture was stirred at ambient temperature for 16 hours and at 50° C. for 4 hours. . The reaction mixture was diluted with ether (150 mL), washed with aqueous 10% $NaHCO_3$ (10 mL), brine (10 mL) and dried with $MgSO_4$. Purification by chromatography on silica gel gave 1.35 g of the title compound as a white solid.

$^1$HNMR ($CDCl_3$): δ1.26 (s, 6H), 2.31 (d, J=4.9 Hz, 2H), 2.52 (s, 3H), 6.15 (t, J=4.9 Hz, 1H), 6.72 (d, J=3.3 Hz, 1H), 6.83 (d, J=3.3 Hz, 1H), 7.21 (d, J=8.3H, 1H), 7.34 (dd, J=2.0, 8.3 Hz, 1H), 7.55 (d, J=2.0 Hz, 1H).

1(5-Methyl-thien-2-yl)3,4-dihydro-4,4-dimethyl-7-naphthaldehyde (Compound G)

To a cold (−78° C.) solution of 1-(5-methyl-thien-2-yl)-3,4-dihydro-4,4-dimethyl-7-bromo-naphthalene (Compound F, 1.35 g, 4.1 mmol), in THF (20 mL) was added t-BuLi in pentane (1.7M solution, 3.5 mL, 5.95 mmol). The reaction was stirred for 15 minutes and DMF (600 mg, 5.8 mmol) was added and dry-ice cooling was replaced with ice-water bath. The mixture was stirred at ambient temperature for 4 hours. The reaction mixture was diluted with ether (70 mL) and washed with water (5 mL), brine (5 mL) and dried with $MgSO_4$. Solvent was removed by distillation. The product was purified by silicagel chromatography to afford the title compound as a colorless oil.

$^1$HNMR ($CDCl_3$): δ1.35 (s, 6H), 2.35 (d, J=4.8 Hz, 2H), 2.52 (s, 3H), 6.20 (t, J=4.8 Hz, 1H), 6.73 (d, J=3.5 Hz, 1H), 6.86 (d, J=3.5 Hz, 1H), 7.52 (d, J=7.9 Hz, 1H), 7.77 (dd, J=1.8, 7.9 Hz, 1H), 7.94 (d, J=1.8 Hz, 1H), 9.93 (s, 1H).

Ethyl 4-[1-(2,2-dimethoxyethyl)-2-{1-(5-methyl-thien-2-yl)3,4-dihydro-4,4-dimethyl-naphthalen-7-yl}-(E)-ethen-1-yl]-benzoate (Compound H)

To a cold (−78° C.) solution of ethyl 4-(diethoxyphosphoryl-3,3-dimethoxypropyl)benzoate (Compound D, 1.4 g, 3.6 mmol), in THF (20 mL) was added n-BuLi (1.6 M solution in hexane, 2.5 mL, 4 mmol). The mixture was stirred for 20 minutes at −78° C. and 10 min. at −10° C. The reaction mixture was recooled to −78° C. and 1(5-methyl-thien-2-yl)3,4-dihydro-4,4-dimethyl-7-naphthaldehyde (Compound G, 650 mg, 2.3 mmol) in THF (4 mL) was added to it. The mixture was stirred for 2 hours at −10° C. and diluted with ether (100 mL), washed with brine (10 mL) dried with $MgSO_4$ and the solvent was removed by distillation to afford a cis and trans (E and Z) isomeric mixture. Purification by chromatography on silica gel of the crude material afforded the title compound as an oil (~90% purity).

$^1$HNMR ($CDCl_3$): δ1.33 (s, 6H), 1.41 (t, J=7.1 Hz, 3H), 2,32 (d, J=4.9 Hz, 2H), 2.49 (s, 3H), 3.06 (d, J=5.7 Hz, 2H), 3.16 (s, 3H), 4.32 (t, J=5.7 Hz, 1H), 4.39 (q, J=7.1 Hz, 2H), 6.13 (t, J=4.9 Hz, 1H), 6.70 (d, J=3.5 Hz, 1H), 6.78 (s, 1H), 6.85 (d, J=3.5 Hz, 1H), 7.37 (d, J=8.0 Hz, 1H), 7.43 (dd, J=1.7, 8.0 Hz, 1H), 7.50 (d, J=8.3 Hz, 3H), 8.02 (d, J=8.3 Hz, 2H).

Ethyl 4-[1(5-methyl-thien-2-yl)3,4-dihydro-4,4-dimethyl-anthracen-8-yl]-benzoate (Compound 3)

To a cold (−50° C.) solution of ethyl 4-[1-(2,2-dimethoxyethyl)-2-{1(5-methyl-thien-2-yl)3,4-dihydro-4,4-dimethyl-naphthalen-7-yl}-(E)-ethenyl]-benzoate (Compound H, 130 mg, 0.25 mmol), in dichloromethane (5 mL) was added $SnCl_4$ (22 mg, in 0.1 mL dichloromethane). After 15 min. the reaction was quenched by adding solid $NaHCO_3$ (100 mg) followed by aqueous 10% $NaHCO_3$ (5 mL), and the resulting mixture was extracted with ether (60 mL). The organic layer was washed with water (5 mL), brine (5 mL) dried with $MgSO_4$ and the solvent was removed by distillation. The product was purified by silicagel chromatography to afford the title compound as a white solid.

$^1$HNMR ($CDCl_3$): δ1.43 (t, J=7.1 Hz, 3H), 1.44 (s, 6H), 2.40 (d, J=4.8 Hz, 2H), 2.56 (s, 3H), 4.41 (q, J=7.1 Hz, 2H), 6.25 (t, J=4.8 Hz, 1H), 6.77 (d, J=3.4 Hz, 1H), 6.96 (d, J=3.4 Hz, 1H), 7.71 (dd, J=1.7, 8.4 Hz, 1H), 7.76 (d, J=8.5 Hz, 2H), 7.78 (s, 1H), 7.88 (d, J=8.4 Hz, 1H), 7.95 (brs, 1H), 7.99 (brs, 1H), 8.12 (d, J=8.4 Hz, 2H).

4-[1(5-Methyl-thien-2-yl)3,4-dihydro-4,4-dimethyl-anthracen-8-yl]-benzoic acid (Compound 4)

To a stirred solution of ethyl 4-[1-(5-methyl-thien-2-yl)-3,4-dihydro-4,4-dimethyl-anthracen-8-yl]-benzoate (Compound 3, 33 mg, 0.07 mmol), in THF (2 mL), MeOH (2 mL), was added aqueous LiOH (1M solution, 0.2 mL, 0.2 mmol). After 16 hours, water (2 mL) was added to the reaction mixture, about 50% of the organic solvents were removed by distillation, and the mixture was further diluted the mixture with water (5 mL). The reaction mixture was washed with ether (10 mL) and the aqueous layer was acidified to pH 4 and extracted with ethyl acetate (3×20 mL). The combined organic layers were washed water (5 mL), brine (10 mL), dried with $MgSO_4$ and the solvent was removed by distillation. The product was recrystallized from acetone to obtain the title compound as a white solid.

$^1$HNMR ($CDCl_3$): δ1.44 (s, 6H), 2.40 (d, J=4.9 Hz, 2H), 2.56 (s, 3H), 6.24 (t, J=4.9 Hz, 1H), 6.79 (d, J=3.4 Hz, 1H), 6.96 (d, J=3.4 Hz, 1H), 7.23 (dd, J=1.7, 8.4 Hz, 1H), 7.79 (brs, 1H), 7.80 (d, J=8.4 Hz, 2H), 7.88 (d, J=8.4 Hz, 1H), 7.96 (s, 1H), 8.01 (s, 1H), 8.18 (d, J=8.4 Hz, 2H).

1-(6-Methyl-pyrid-3-yl)-3,4-dihydro-4,4-dimethyl-7-bromo-naphthalene (Compound I)

To a cold (−78° C.) solution of 6-methyl-3-bromopyridine (890 mg, 5.2 mmol) in THF (15 mL) was added n-BuLi in hexane (1.6M solution, 3.5 mL, 5.6 mmol) and stirred for 1 hour. This mixture was added to a flask containing 3,4-dihydro-4,4-dimethyl-7-bromo-1(2H)-naphthalenone (Compound A, 1.35 g, 5.4 mmol), in THF (5 mL) at −78° C. The reaction mixture was gradually warmed to ambient temperature and stirred for 16 hours. Thereafter it was diluted with ethyl acetate (100 mL), washed with water (10 mL), brine (10 mL) and dried with $MgSO_4$. Solvent was removed by distillation, the crude material was dissolved in toluene (25 mL) and pTSA (530 mg, 2.8 mmol) was added. The mixture was heated at 90° C. for 36 hours. Thereafter it was diluted with ethyl acetate (100 mL), washed with 10% $NaHCO_3$ (2×10 mL), brine (10 mL), dried with $MgSO_4$ and the solvent was removed by evaporation. The title compound was obtained by recrystallization from ethyl acetate and hexane mixture (1:9).

$^1$HNMR ($CDCl_3$): δ1.31 (s, 6H), 2.34 (d, J=4.7 Hz, 2H), 2.60 (s, 3H), 6.02 (t, J=4.7 Hz, 1H), 7.05 (d, J=2.1 Hz, 1H), 7.17 (d, J=7.8 Hz, 1H), 7.21 (d, J=8.3 Hz, 1H), 7.34 (dd, J=2.1, 8.2 Hz, 1H), 7.51 (d, J=2.3, 8.3 Hz, 1H), 8.46 (d, J=2.3 Hz, 1H).

Ethyl1-(6-methyl-pyrid-3-yl)3,4-dihydro-4,4-dimethyl-7-naphthoate (Compound J)

Carbon monoxide gas was bubbled for 5 minutes through a mixture of 1-(6-methyl-pyrid-3-yl)3,4-dihydro-4,4-dimethyl-7-bromo-naphthalene (Compound J, 250 mg, 0.75 mmol), $Et_3N$ (5 mL), MeOH (10 mL), DMSO (10 mL), $Pd(PPh_3)_2Cl_2$ (70 mg, 0.1 mmol) and 1,3-bis(diphenylphophino)propane (206mg, 0.5 mmol). The mixture was heated to 50° C. for 16 hours under a carbon monoxide atmosphere (carbon monoxide balloon). Thereafter solvent was distilled off, water (15 mL) was added, and the mixture was extracted with ethyl acetate (3×40 mL). The combined organic layers were washed with water (10 mL), brine (10 mL) dried with $MgSO_4$ and the solvent was removed by evaporation. The crude material was purified by silicagel column chromatography to afford the title compound as a white solid.

$^1$HNMR (CDCl$_3$): δ1.33 (s, 6H), 2.35 (d, J=4.9 Hz, 2H), 2.59 (s, 3H), 3.80 (s, 3H), 6.03 (t, J=4.9 Hz, 1H), 7.16 (d, J=8.0 Hz, 1H), 7.41 (d, J=8.0 Hz, 1H), 7.51 (dd, J=2.2, 8.0 Hz, 1H), 7.60 (d, J=1.8 Hz, 1H), 7.89 (dd, J=1.8, 8.0 Hz, 1H), 8.47 (d, J=2.2 Hz, 1H).

16(6-methyl-pyrid-3-yl)3,4-dihydro-4,4-dimethyl-naphthaldehyde (Compound K)

To a cold (−78° C.) solution of methyl 1-(6-methyl-pyrid-3-yl)3,4-dihydro-4,4-dimethyl-7-naphthoate (Compound J, 200 mg, 0.65 mmol), in dichloromethane (4 mL) was added DiBAl-H in dichloromethane (1M solution, 2 mL, 2 mmol). The mixture was stirred for 2 hours, quenched with aq. KOH solution (100 mg in 2 mL), and a gel precipitate formed. The mixture was transferred to a seperatory funnel, and was extracted with ethyl acetate (3×30 mL). The combined organic layers were washed with brine (10 mL), dried with MgSO$_4$, and the solvent was removed by evaporation. The crude product was dissolved in dichloromethane (10 mL), MnO$_2$ (650 mg, 7.5 mmol) was added and the mixture was stirred for 6 hours. The solid was filtered off, and the solvent was removed to afford the title compound as a white solid.

$^1$HNMR (CDCl$_3$): δ1.38 (s, 6H), 2.41 (d, J=4.7 Hz, 2H), 2.63 (s, 3H), 6.09 (t, J=4.7 Hz, 1H), 7.21 (d, J=8.0 Hz, 1H), 7.44 (d, J=1.8 Hz, 1H), 7.51–7.59 (m, 3H), 7.77 (dd, J=1.8, 8.0 Hz, 1H), 8.49 (d, J=1.8 Hz, 1H), 9.86 (s, 1H).

Ethyl 4-[1-(6-methyl-pyrid-3-yl)-3,4-dihydro-4,4-dimethyl-anthracen-8-yl]-benzoate (Compound 5)

This compound is prepared in accordance with the procedure described for the preparation of ethyl 4-[1(5-methyl-thien-2-yl)3,4-dihydro-4,4-dimethyl-anthracen-8-yl]-benzoate (Compound 3), from 1(2-methyl-pyrid-5-yl)3,4-dihydro-4,4-dimethyl-naphthaldehyde (Compound K) by reaction with ethyl 4-(diethoxyphosphoryl-3,3-dimethoxypropyl)benzoate (Compound D) and proceeding through the intermediate ethyl 4-[1-(2,2-dimethoxyethyl)-2-{1-(tol-4-yl)3,4-dihydro-4,4-dimethyl-naphthalen-7-yl}-(E)-ethen-1-yl]-benzoate which is cyclized by treatment with SnCl$_4$ in dichloromethane to give the title compoud.

4-[1(6-methyl-pyrid-5-yl)-3,4-dihydro-4,4-dimethyl-anthracen-8-yl]-benzoic acid (Compound 6)

The title compound is obtained by saponification with LiOH of ethyl 4-[1(tol-4-yl)-3,4-dihydro-4,4-dimethyl-anthracen-8-yl]-benzoate (Compound 5) in accordance with the procedure described for the preparation of 4-[1(5-methyl-thien-2-yl)3,4-dihydro-4,4-dimethyl-anthracen-8-yl]-benzoic acid (Compound 4).

3-Methyl-3-(4-bromo-thiophenyl)butyric acid (Compound L)

A mixture of 4-bromothiophenol (9.5 g, 50 mmol), 3,3-dimethylacrylic acid (5 g, 50 mmol) and piperidine were heated (110° C.) in a screw cap heavy walled tube covered with teflon cap. The reaction mixture became a thick liquid after 30 minutes of heating. Heating was continued for 23 hours. Then the mixture was cooled to ambient temperature, and solved in ethyl acetate (200 mL). The mixture was washed with 10% aq. HCl, water (50 mL), brine (50 mL) and dried with MgSO$_4$. Solvent was removed and the crude product was recrystallized from hexane to afford the title compound as a colorless solid.

$^1$HNMR (CDCl$_3$): δ1.42 (s, 6H), 2.55 (s, 2H), 7.43 (d, J=8.6 Hz, 2H), 7.49 (d, J=8.6 Hz, 2H).

2.2-Dimethyl-6-bromo-thiochroman-4-one (Compound M)

To a solution of 3-methyl-3-(4-bromo-thiophenyl)butyric acid (Compound L, 9.1 g, 33.4 mmol) in benzene (125 mL) was added oxalyl chloride (7.4 g, 59 mmol). The mixture was stirred for 5 hours at ambient temperature, and thereafter washed with ice-cold 5% NaOH (100 mL), ice-cold water (2×50 mL) and brine (50 mL). The organic layer was dried with MgSO$_4$ and the solvent was removed by distillation. The residual colorless oil was dissolved in dichloromethane (50 mL), cooled to 0° C. and SnCl$_4$ (14.7 g, 57 mmol) was added. The mixture was stirred at ambient temperature for 14 hours, and poured into ice. The mixture was extracted with ethyl acetate, washed with 10% NaOH, water, brine, dried with MgSO$_4$ and the solvent was removed by distillation. The crude material was purified by silicagel chromatography and after standing at ambient temperature for overnight crystalline product was collected by filtration.

$^1$HNMR (CDCl$_3$): δ1.46 (s, 6H), 2.87 (s, 2H), 7.12 (d, J=8.4 Hz, 2H), 7.50 (dd, J=2.2, 8.4 Hz, 1H), 8.22 (d, J=2.2 Hz, 1H).

2,2-Dimethyl-4(tol-4-yl)-6-bromo-thiochrom-3-ene (Compound N)

To a cold (−78° C.) solution of 4-bromotoluene (720 mg, 4.2 mmol) in THF (8 mL) was added t-BuLi in pentane (1.7M, 0.5 mL, 0.85 mmol). The mixture was warmed to ambient temperature over 30 minutes with stirring. This mixture was added to a flask containing 2,2-dimethyl-6-bromo-thiochroman-4-one (Compound M, 140 mg, 0.4 mmol) and THF (2 mL). and stirred for 16 hours at ambient temperature. The reaction was quenched by adding aq. NH$_4$Cl, and the resulting mixture was extracted with ethylacetate, washed with brine, dried and the solvent was removed by evaporation. The product was isolated by chromatography on silica gel. The material was dissolved in dichloromethane (5 mL) and pTSA (5 mg) was added and heated to 50° C. for 3 hours. The misture was diluted with ethylacetate (20 mL), washed with 10% NaHCO$_3$ (5 mL), brine (5 mL), dried with MgSO$_4$ and the solvent was removed by evaporation to afford the title compound as an oil.

$^1$HNMR (CDCl$_3$): δ1.46 (s, 6H), 2.40 (s, 3H), 5.84 (s, 1H), 7.12–7.29 (m, 7H).

2,2-Dimethyl-4(tol-4-yl)-thiochrom-3-en-6-al (Compound O)

To a cold (−78° C.) solution of 2,2-dimethyl-4(tol-4-yl)-6-bromo-thiochrom-3-ene (Compound N, 280 mg, 0.81 mmol) in THF (5 mL) was added n-BuLi in hexane (1.6 M solution, 0.66 mL). The mixture was gradually warmed to −10° C. over 25 min. and recooled to −78° C. To this solution was added DMF (80 mg, 1.1 mmol) and stirred at ambient temperature for 5 hours. The reaction was quenched by adding water (10 mL), ethyl acetate (100 mL), and the organic layer was washed with brine (10 mL), dried and the solvent removed by distillation. The crude material was used in the next reaction without further purification.

Ethyl 4-[2,2-dimethyl-4-(tol-4-yl)-6,7-benzothiochrom-3-en-7-yl]benzoate (Compound 7)

To a cold (−78° C.) solution of ethyl 4-(diethoxyphosphoryl-3,3-dimethoxypropyl)benzoate (Compound D, 536 mg, 1.4 mmol) in THF (5 mL) was added n-BuLi in hexane (1.6 M solution, 1.2 mL) and stirred for 1 hour between −78° C. and −10° C. The mixture was cooled to −78° C. and 2,2-dimethyl-4(tol-4-yl)-thiochrom-3-en-6-al (Compound O, as obtained in the previously described reaction) in THF (1 mL) was added to it. The reaction mixture was stirred at ambient temperature for 1 hour and diluted with ethyl acetate (60 mL), washed with brine (10 mL), dried and the solvent was removed by evaporation. The crude material was purified by column chromatography to afford the E and Z isomers as a mixture. The mixture of E and Z isomers was dissolved in dichloromethane (4 mL) and cooled to −78° C. To the cold solution was added SnCl4 (110 mg, 0.42 mmol) in dichloromethane (1 mL). The reaction mixture was stirred between −78° C. and −30° C. for 30 minutes and then quenched with ethanol (0.2 mL), diluted with ethyl acetate (30 mL), washed with brine, dried and the solvent was removed by distillation. The crude material was purified by column chromatography to obtain the title compound as a white solid.

$^1$HNMR (CDCl$_3$): d 1.43 (t, J=7.2 Hz, 3H), 1.53 (s, 6H), 2.44 (s, 3H), 4.41 (q, J=7.2 Hz, 2H), 6.02 (s, 1H), 7.21–7.31 (m, 4H), 7.59 (s, 1H), 7.69–7.75 (m, 3H), 7.80 (d, J=8.5 Hz, 1H), 7.88 (s, 2H), 8.11 (d, J=8.3 Hz, 2H).

4-[2,2-dimethyl-4-(tol-4-yl)-6,7-benzothiochrom-3-en-7-yl]benzoic acid (Compound 8)

To an argon purged solution of ethyl 4-[2,2-dimethyl-4-(tol-4-yl)-6,7-benzothiochrom-3-en-7-yl]benzoate (Compound 7, 12 mg, 0.03 mmol), THF (2 mL) and MeOH (1 mL) was added LiOH in water (1M solution, 0.2 mL) and purged (with argon) for 2 minutes. The mixture was stirred for 16 hours at ambeint temperature. The reaction mixture was acidified with 10% hydrochloric acid to pH 4, extracted with ethyl acetate (35 mL), washed with brine, dried and the solvent was removed by distillation. The title compound was obtained as an off white solid.

$^1$HNMR (Acetone-D6): d 1.50 (s, 6H), 2.39 (s, 3H), 6.08 (s, 1H), 7.26 (s, 4H), 7.84–7.96 (m, 5H), 8.12 (d, J=8.3 Hz, 3H).

2,2-Dimethyl-4(tol-4-yl)-6-bromo-chrom-3-ene (Compound P)

To cold (−78° C.) solution of 4-bromotoluene (1.71 g, 10 mmol) in THF (16 mL) was added t-BuLi in pentane (1.7M, 3 mL). The mixture was warmed to ambient temperature and stirred for 15 minutes and then recooled to −78° C. To this solution, 2,2-dimethyl-6-bromo-chroman-4-one (750 mg, 3 mmol) in THF (4 mL) was added and stirred for 30 minutes. 2,2-Dimethyl-6-bromo-chroman-4-one is available in accordance with the procedure of Bickle et al. J. Med. Chem. 1990 33 p3028. The reaction was quenched with water (5 mL), extracted with ethyl acetate (10 mL), washed with brine, dried and the solvent was removed by evaporation. Chromatography of the crude mixture afforded 2,2-dimethyl-4-tolyl-4-hydoxy-6-bromo-chroman an oil. This product was dissolved in dichloromethane (25 mL), and pTSA (25 mg) was added and the mixture stirred for 12 hours. The mixture was then diluted with ethyl acetate (125 mL), washed with 10% NaHCO$_3$ (10 mL), brine, dried and the solvent was removed by evaporation to afford the title compound as a yellow oil.

$^1$HNMR (CDCl$_3$): δ1.48 (s, 6H), 2.41 (s, 3H), 5.61 (s, 1H), 6.76 (d, J=8.3 Hz, 1H), 7.11 (d, J=2.4 Hz, 1H), 7.22 (s, 4H), 7.26 (dd, J=2.4, 8.3 Hz, 1H).

2,2-Dimethyl-4(tol-4-yl)-chrom-3-en-6-al (Compound Q)

To a cold (−78° C.) solution of 2,2-dimethyl-4(tol-4-yl)-6-bromo-chrom-3-ene (Compound P, 480 mg, 1.45 mmol) in THF (10 mL), was added t-BuLi in pentane (1.7M solution, 1.1 mL) and the mixture was stirred for 30 minutes. DMF (200 mg, 2.9 mmol) was added, the mixture was warmed to ambient temperature and stirred for 3 hours. The reaction was diluted with ethyl acetate (150 mL), washed with brine (10 mL), dried and the solvent was removed by evaporation. Purification by chromatography on silica gel column gave the title compound as a colorless oil.

$^1$HNMR (CDCl$_3$): δ1.54 (s, 6H), 2.41 (s, 3H), 5.66 (s, 1H), 6.98 (d, J=8.3 Hz, 1H), 7.24 (s, 4H), 7.57 (d, J=2.0 Hz, 1H), 7.71 (dd, J=2.0, 8.3 Hz, 1H), 9.77 (s, 1H).

Ethyl-4-[2,2-dimethyl-4-(tol-4-yl)-benzo[1,2-g]-chrom-3-en-7-yl]benzoate (Compound 9)

To a cold (−78° C.) solution of ethyl 4-(diethoxyphosphoryl-3,3-dimethoxypropyl)benzoate (Compound D, 1.4 g, 3.6 mmol) in THF (9 mL) was added n-BuLi in hexane (1.6 M solution, 2.8 mL). The mixture was gradually warmed to ambient temperature over 30 minutes and stirred for 5 minutes. To this mixture was added 2,2-dimethyl-4(tol-4-yl)-chrom-3-en-6-al (Compound Q, 260 mg, 0.93 mmol) in THF (1 mL) at ambient temperature and the mixture was stirred for 5 hours. The reaction mixture was diluted with ethyl acetate (100 mL) and washed with brine (10 mL) dried and the solvent was removed by evaporation. The residual material was subjected to flash chromatography on silicagel to obtain the E and Z olefinic compounds, which were dissolved in dichloromethane (5 mL) and cooled to −50° C. A solution of SnCl$_4$ in dichloromethane (150 mg in 0.7 mL) was added to the olefinic compounds. The reaction mixture was gradually warmed to −10° C. over 3 hours and then quenched with methanol and water. The reaction mixture was diluted with ethyl acetate (100 mL). The organic layer was washed with brine and dried. Solvent was removed under reduced pressure and the residue purified by chromatography on silicagel to afford the title compound as a white solid.

$^1$HNMR (CDCl$_3$): δ1.43 (t, J=7.1 Hz, 3H), 1.55 (s, 6H), 2.45 (s, 3H), 4.41 (q, J=7.1 Hz, 2H), 5.85 (s, 1H), 7.24–7.38 (m, 5H), 7.53 (s, 1H), 7.65–7.78 (m, 4H), 7.88 (s, 1H), 8.11 (d, J=8.5 Hz, 2H).

4-[2,2-Dimethyl-4-(tol-4-yl)-benzo(1,2-g)-chrom-3-en-7yl]benzoic acid (Compound 10)

By following the procedure employed for the preparation of 4-[1(5-methyl-thien-2-yl)3,4-dihydro-4,4-dimethyl-anthracen-8-yl]-benzoic acid (Compound 4), ethyl 4-[2,2-dimethyl-4-(tol-4-yl)-benzo(1,2-g)-chrom-3-en-7-yl]benzoate (Compound 9, 10 mg, 0.02 mmol), was converted into the title compound using LiOH in water (0.2 mL, 0.2 mmol). The title compound was obtained as an off white solid.

$^1$HNMR (Acetone-D6): d 1.52 (s, 6H), 2.41 (s, 3H), 5.96 (s, 1H), 7.27–7.38 (m, 4H), 7.60 (s, 1H), 7.78–7.86 (m, 3H), 7.90 (d, J=8.2 Hz, 2H), 8.10 (d, J=8.2 Hz, 2H), 8.11 (s, 1H).

2,2-Dimethyl-4(5-methyl-thien-2-yl)-6-bromo-chrom-3-ene (Compound R)

To a cold (−78° C.) solution of 2-methylthiophene (820 mg, 8.3 mmol) in THF (16 mL) was added n-BuLi in hexane (1.6M, 4.4 mL, 8.5 mmol). The mixture was warmed to ambient temperature and stirred for 15 minutes. This solution was added to a flask containing cold (−78° C.) solution of 2,2-dimethyl-6-bromo-chroman-4-one (1.08 g, 4.2 mmol) in THF (4 mL). The mixture was stirred and allowed to gradually warm to ambient temperature over 8 hours, and then stirred for an additional 4 hours at ambient temperature. The mixture was diluted with ethyl acetate (200 mL), washed with 10% HCl, brine (20 mL), dried and the solvent was removed by evaporation. The product was purified by chromatography on a silica gel column to afford the title compound as a colorless oil.

$^1$HNMR (CDCl$_3$): δ1.46 (s, 6H), 2.52 (s, 3H), 5.75 (s, 1H), 6.73 (brs, 1H), 6.76 (d, J=8.4 Hz, 1H), 6.88 (d, J=2.5 Hz, 1H), 7.26 (dd, J=2.5, 8.4 Hz, 1H), 7.48 (d, J=2.4 Hz, 1H).

2,2-Dimethyl-4(5-methyl-thien-2-yl)-chrom-3-en-6-al (Compound S)

To a cold (−78° C.) solution of 2,2-dimethyl-4(5-methyl-thien-2-yl)-6-bromo-chrom-3-ene (Compound R, 1.2 g, 3.6 mmol) in THF (10 mL), was added t-BuLi in pentane (1.7M solution, 2.3 mL). After 30 minutes, DMF (465 mg, 5 mmol) was added and the mixture was allowed to warm to ambient temperature and stirred for 3 hours. The mixture was diluted with ethyl acetate (150 mL), washed with brine (10 mL), dried and the solvent was removed by evaporation. Purification by chromatography on silica gel column gave the title compound as a colorless oil.

$^1$HNMR (CDCl$_3$): δ1.51 (s, 6H), 2.52 (s, 3H), 5.80 (s, 1H), 6.75 (d, J=2.7 Hz, 1H), 6.91 (d, J=2.7 Hz, 1H), 6.97 (d, J=8.3 Hz, 1H), 7.73 (dd, J=2.0, 8.3 Hz, 1H), 7.94 (d, J=2.0 Hz, 1H), 9.83 (s, 1H).

Ethyl-4-[2,2-dimethyl-4-(5-methyl-thien-2-yl)-benzo[1,2-g]-chrom-3-en-7-yl]benzoate (Compound 11)

To a cold (−78° C.) solution of ethyl 4-(diethoxyphosphoryl-3,3-dimethoxypropyl)benzoate (Compound D, 690 mg, 1.75 mmol) in THF (8 mL) was added n-BuLi in hexane (1.6 M solution, 1.1 mL). The mixture was gradually warmed to ambient temperature over 30 min and stirred for 5 minutes. The mixture was recooled to −78° C. and 2,2-dimethyl-4(5-methyl-thien-2-yl)-chrom-3-en-6-al (Compound S, 300 mg, 1.1 mmol) in THF (1 mL) was added to the reaction mixture. The mixture was stirred at ambient temperature for 2 hours. The reaction mixture was diluted with ethyl acetate (100 mL) and washed with brine (10 mL) dried and the solvent was removed by evaporation. The material was subjected to flash chromatography on silica gel to obtain the E and Z olefinic compounds, which were dissolved in dichloromethane (5 mL) and cooled to −78° C. A solution of SnCl$_4$ in dichloromethane (52 mg in 0.2 mL) was added to the olefinic compounds. The resulting mixture was stirred for 30 minutes, quenched with methanol, water and diluted with ethyl acetate (100 mL). The organic layer was washed with brine and dried. Solvent was removed under reduced pressure and purified by silicagel chromatography to afford the title compound as a white solid.

$^1$HNMR (CDCl$_3$): δ1.43 (t, J=7.1 Hz, 3H), 1.53 (s, 6H), 2.56 (s, 3H), 4.41 (q, J=7.1 Hz, 2H), 5.99 (s, 1H), 6.79 (d, J=3.5 Hz, 1H), 7.00 (d, J=3.5 Hz, 1H), 7.29 (s, 1H), 7.68 (dd, J=1.8, 8.5 Hz, 1H), 7.72–7.79 (m, 3H), 7.93 (s, 1H), 7.97 (s, 1H), 8.14 (d, J=8.5 Hz, 2H).

4-[2,2-Dimethyl-4-(5-methyl-thien-2-yl)-benzo[1,2-g]-chrom-3-en-7-yl]benzoic acid (Compound 12)

To a solution of ethyl-4-[2,2-dimethyl-4-(5-methyl-thien-2-yl)-benzo[1,2-g]-chrom-3-en-7-yl]benzoate (Compound 11, 18 mg, 0.03 mmol) in methanol (0.5 mL) and THF (1 mL), was added LiOH in water (1M solution, 0.3 mL). The reaction mixture was stirred for 20 hours, the solvent was removed under reduced pressure, the residue dissolved in water (5 mL), washed with ether (10 mL) and the aqueous layer was acidified to PH 5. The aqueous layer was extracted with ethyl acetate (3×20 mL). The combined organic layers were washed with brine, dried, and the solvent was removed under reduced pressure to afford the title compound as a pale yellow solid.

$^1$HNMR (CH$_3$COCH$_3$): δ1.50 (s, 6H), 2.52 (s, 3H), 6.11 (s, 1H), 6.85 (brs, 1H), 7.07 (d, J=3.3 Hz, 1H), 7.31 (s, 1H), 7.80–7.90 (m, 2H), 7.91 (d, J=8.4, 2H), 8.01 (s, 1H), 8.12 (d, J=8.4 Hz, 2H), 8.19 (s, 1H).

2,2-Dimethyl-4(2-methyl-thien-5-yl)-6-bromo-thiochrom-3-ene (Compound T)

To a cold (−78° C.) solution of 2-methylthiophene (1.2 g, 12.2 mmol) in THF (8 mL) was added n-BuLi in hexane (1.6M, 8.5 mL). The mixture was warmed to ambient temperature over 30 minutes with stirring. The mixture was recooled to −78° C. and a solution of 2,2-dimethyl-6-bromo-thiochroman-4-one (Compound M, 1.4 g, 5.2 mmol) in THF (10 mL) was added. The mixture was stirred for 16 hours at ambient temperature. Then the reaction mixture was diluted with ether (125 mL), washed with water (10 mL), brine (10 mL) dried and the solvent was removed by evaporation. The product was seperated by column chromatography and was dissolved in dichloromethane (5 mL). To this solution p-TSA (5 mg) was added and the mixture was stirred at ambient temperature for 5 min. The reaction was quenched with 10% NaHCO$_3$ (3 mL), washed with brine (5 mL), dried and the solvent was removed by distillation. The residual crude material was purified by column chromatography to obtain the title compound as a pale yellow oil.

$^1$HNMR (CDCl$_3$): d 1.44 (s, 6H), 2.51 (s, 3H), 6.00 (s, 1H), 6.72 (d, J=1.1 Hz, 1H), 6.79 (d, J=1.1 Hz, 1H), 7.23 (d, J=8.2 Hz, 1H), 7.29 (dd, J=2.1, 8.2 Hz, 1H), 7.58 (d, J=2.1 Hz, 1H).

2,2-Dimethyl-4(2-methyl-thien-5-yl)-thiochrom-3-en-6-al (Compound U)

To a cold (−78° C.) solution of 2,2-dimethyl-4(2-methyl-thien-5-yl)-6-bromo-thiochrom-3-ene (Compound T, 430 mg, 1.2 mol) in THF (12 mL) was added n-BuLi in hexane (1.6 M solution, 1 mL). The mixture was gradually warmed to ambient temperature over 1 hour and recooled to −78° C. To this solution was added DMF (220 mg, 3 mmol) and the mixture was stirred at ambient temperature for 16 hours. The reaction was quenched by adding water (10 mL) and ethyl acetate (100 mL). The organic layer was washed with brine (10 mL), dried and the solvent was removed by distillation to obtain the title compound as a pale yellow oil.

$^1$HNMR (CDCl$_3$): d 1.47 (s, 6H), 2.51 (s, 3H), 6.03 (s, 1H), 6.72 (d, J=2.5 Hz, 1H), 6.80 (d, J=2.5 Hz, 1H), 7.49 (d, J=8.1 Hz, 1H), 7.68 (dd, J=1.7, 8.1 Hz, 1H), 7.95 (d, J=1.7 Hz, 1H), 9.88 (s, 1H).

Ethyl 4-[2,2-dimethyl-4-(2-methyl-thien-5-yl)-6,7-benzothiochrom-3-en-7-yl]benzoate (Compound 13)

To a cold (−78° C.) solution of ethyl 4-(diethoxyphosphoryl-3,3-dimethoxypropyl)benzoate (Compound D, 500 mg, 1.29 mmol) in THF (2.5 mL) was added freshly prepared lithium diisopropylamide in THF(1.5 mmol). The mixture was allowed to warm to −5° C. over a period of 1 hour and 40 minutes. The reaction mixture was recooled to −78° C. and 2,2-dimethyl-4(2-methyl-thien-5-yl)-thiochrom-3-en-6-al (Compound U, 180 mg, 0.58 mmol) in THF (2 mL) was added. The reaction mixture was gradually warmed to −10° C. over 2 hours. Then the reaction was quenched by adding water (5 mL) and ethyl acetate (70 mL). The organic layer was washed with brine (10 mL) dried and the solvent was removed by distillation. The product E and Z isomers were isolated by column chromatography. The required E (minor) isomer (45 mg) was dissolved in dichloromethane (5 mL) and cooled to −78° C. To this solution $SnCl_4$ (110 mg, 0.42 mmol) in dichloromethane (1 mL) was added dropwise, the reaction mixture was gradually warmed to −30° C. over 30 min. The reaction was quenched by adding ethanol (0.5 mL), water (5 mL) and ethyl acetate (75 mL). The organic layer was washed with brine (10 mL), dried and the solvent was removed by distillation. The title compound was isolated as a white solid after column chromatography.

$^1$HNMR ($CDCl_3$) d 1.43 (t, J=7.1 Hz, 3H), 1.55 (s, 6H), 2.55 (s, 3H), 4.42 (q, J=7.1 HZ, 2H), 6.19 (s, 1H), 6.75 (d, J=1.9 Hz, 1H), 6.90 (d, J=1.9 Hz, 1H), 7.70–7.85 (m, 4H), 7.87 (s, 1H), 7.97 (s, 1H), 8.00 (s, 1H), 8.12 (d, J=8.4 Hz, 2H).

4-[2,2-Dimethyl-4-(2-methyl-thien-5-yl)-benzo(1,2-g)-thiochrom-3-en-7-yl]benzoic acid (Compound 14)

To a degassed solution of ethyl 4-[2,2-dimethyl-4-(2-methyl-thien-5-yl)-benzo(1,2-g)-thiochrom-3-en-7-yl] benzoate (Compound 13, 28 mg, 0.06 mmol), in THF (2 mL) and MeOH (1 mL) was added LiOH (1M solution in water, 0.2 mL) and the mixture was stirred for 16 hours. The reaction was acidified to pH 4 and extracted with ethyl acetate (50 mL). The organic layer was washed with brine, dried and the solvent was removed to afford the title compound as a pale yellow solid.

$^1$HNMR ($CDCl_1$): d 1.52 (s, 6H), 2.55 (s, 3H), 6.19 (s, 1H), 6.74 (d, J=1.9 Hz, 1H), 6.90 (d, J=1.9 Hz, 1H), 7.71–7.85 (m, 4H), 7.88 (s, 1H), 7.97 (s, 1H), 8.00 (s, 1H), 8.12 (d, J=8.4 Hz, 2H).

What is claimed is:

1. A compound of the formula

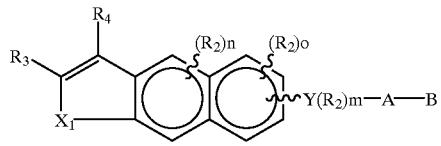

wherein $X_1$ is —S—, or —O—;
$R_1$ is independently H or alkyl of 1 to 6 carbons;

$R_2$ is optional and is defined as lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer between 0 and 4;

n is an integer between 0 and 2;

o is an integer between 0 and 3;

$R_3$ is hydrogen, lower alkyl of 1 to 6 carbons, F, Cl, Br or I;

$R_4$ is heteroaryl or $(R_5)_p$-heteroaryl where the heteroaryl group is 5-membered or 6-membered and has 1 to 3 heteroatoms selected from the group consisting of O, S and N, with the proviso that heteroaryl is not pyridyl nor thienyl;

p is an integer having the values of 0–5;

$R_5$ is independently F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl or (trialkyl)silyloxy group where the alkyl groups independently have 1 to 6 carbons;

Y is pyridyl said pyridyl group being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound in accordance with claim 1 where the A—B group is $(CH_2)_n$—COOH or $(CH_2)_n$—$COOR_8$ or a pharmaceutically acceptable salt thereof.

3. A compound in accordance with claim 2 where n is zero.

* * * * *

UNITED STATES PATENT AND TRADEMARK OFFICE
CERTIFICATE OF CORRECTION

PATENT NO.   : 6,087,505
DATED        : July 11, 2000
INVENTOR(S)  : Vuligonda et al.

It is certified that error appears in the above-identified patent and that said Letters Patent is hereby corrected as shown below:

Title page, Item [54] and Column 1, Line 1,
Title, insert -- ARYL OR HETEROARYL SUBSTITUTED 3,4-DIHYDROANTHRACENE AND ARYL OR HETEROARYL SUBSTITUTED -- before "BENZO".

Title page,
Item [56], References Cited, FOREIGN PATENT DOCUMENTS, "170105" should be -- 170105A --; insert -- C07F -- after "0303186  2/1989  European Pat. Off."; "403/20" should be -- 231/54 --; and "231/54" should be -- 403/20 --.

Column 1,
Line 3, insert -- HAVING RETINOID ANTAGONIST OR RETINOID INVERSE AGONIST TYPE BIOLOGICAL ACTIVITY -- after "DERIVATIVES".
Line 4, "CROSS REFERENCE TO RELATED APPLICATION" should begin a new paragraph as -- 1. Cross-reference to related application. --;
Line 10, BACKGROUND OF THE INVENTION" should precede "1. Cross-reference to related application".
Line 12, "1." should be -- 2. --.
Line 23, should be -- 3. --.

Column 2,
Line 5, "Minoxidil$^R$"" should be -- Minoxidil$^R$, --.
Line 50, "RXB$_\beta$" should be -- RXR$_\beta$ --.

Column 4,
Line 41, "alky" should be -- alkyl --.

Column 5,
Line 22, "Minoxidil$^R$"" should be -- Minoxidil$^R$, --.

Column 6,
Line 19, "RXR$_\Gamma$" should be -- RXR$_\gamma$ --.

Column 9,
Line 55, "mililiter" should be -- milliliter --.

Column 10,
Line 5, "alky" should be -- alkyl --.

UNITED STATES PATENT AND TRADEMARK OFFICE
CERTIFICATE OF CORRECTION

PATENT NO. : 6,087,505
DATED : July 11, 2000
INVENTOR(S) : Vuligonda et al.

It is certified that error appears in the above-identified patent and that said Letters Patent is hereby corrected as shown below:

Column 13,
Line 37, "C." should be -- C --.

Column 14,
Line 46, insert -- , -- after "l".

Column 17,
Line 11, "examplary" should be -- exemplary --.
Line 28, "1509 1516" should be -- 1509-1516 --.

Column 18,
Line 1, "triphenylphoshine" should be -- triphenylphosphine --.
Line 24, "dimetyl" should be -- dimethyl --.
Line 29, "phoshonates" should be -- phosphonates --.
Line 57, "dischloromethane" should be -- dichloromethane --.

Column 20,
Line 15, "$R_{4X2}$" should be -- $R_4$-$X_2$ --.
Line 27, "compond" should be -- compound --.
Line 28, "forula" should be -- formula --.
Line 31, "1,2," should be -- 1,2- --.
Line 33, delete --1 -- after"-g".
Line 50, "substituted" should be -- substituted --.
Line 54, insert -- in -- after the word "available".
Line 66, "-(2H) one" should be -- -(2H)-one --.

Column 24,
Lines 4 and 10, "ethyl)-" should be -- ethyl]- --.

Column 25,
Lines 7, 10, 32 and 52, "C." should be -- C --.

Column 26,
Lines 11, 47, 50 and 59, "C." should be -- C --.
Line 28, insert -- - -- after "Tol".
Line 59, delete the first occurrence of "." after the word "hours".
Line 66, "J=8.3H" should be -- J=8.3 Hz --.

UNITED STATES PATENT AND TRADEMARK OFFICE
CERTIFICATE OF CORRECTION

PATENT NO. : 6,087,505
DATED : July 11, 2000
INVENTOR(S) : Vuligonda et al.

It is certified that error appears in the above-identified patent and that said Letters Patent is hereby corrected as shown below:

Column 27,
Lines 4, 24, 28, 29, 33 and 50, "C." should be -- C --.
Line 30, "1(5" should be -- 1-(5 --.
Line 40, "2,32" should be -- 2.32 --.
Line 47, "[1(5" should be -- [l-(5 --.
Line 51, "{1(5" should be -- {1-(5 --.

Column 28,
Line 11, delete "the mixture" after the word "diluted".
Line 14, insert -- with -- after"washed".
Lines 26, 38 and 59, "C." should be -- C --.
Line 58, "diphenylphophino" should be -- diphenylphosphino --.

Column 29,
Line 7, "16(6" should be -- 1-(6 --.
Lines 9 and 57, "C." should be -- C --.
Line 15, "seperatory" should be -- separatory --.
Line 34, "1(2" should be -- 1-(2 --.
Line 43, "[1(6" should be -- [1-(6 --.
Line 48, "[1(5" should be -- [1-(5 --.

Column 30,
Line 1, "2.2" should be -- 2,2 --.
Lines 12, 27, 40, 51, 55 and 65, "C." should be -- C --.
Line 18, delete "for" after the word "temperature".
Line 33, delete "." after "(2mL)".
Line 40, "misture" should be -- mixture --.

Column 31,
Line 2, the both occurrences of "C." should be -- C --.
Lines 3, 12, 14, 15, 41 and 66, "C." should be -- C --.
Line 13, "SnCl4" should be -- $SnCl_4$ --.
Lines 19 and 35, "d" should be -- δ --.
Line 30, "ambeint" should be -- ambient --.
Line 53, "hydoxy" should be -- hydroxy --.

Column 32,
Lines 16, 32, 61 and 65, "C." should be -- C --.
Line 54, "d" should be -- δ --.

UNITED STATES PATENT AND TRADEMARK OFFICE
CERTIFICATE OF CORRECTION

PATENT NO. : 6,087,505
DATED : July 11, 2000
INVENTOR(S) : Vuligonda et al.

It is certified that error appears in the above-identified patent and that said Letters Patent is hereby corrected as shown below:

Column 33,
Lines 16, 33, 39 and 48, "C." should be -- C --.

Column 34,
Line 5, "PH" should be -- pH --.
Lines 18, 22, 44, 63 and 67, "C." should be -- C --.
Line 28, "separated" should be -- separated --.
Line 36, "d" should be -- δ --.
Line 46, "mol" should be -- mmol --.
Line 51, "ethy lacetate" should be -- ethyl acetate --.
Line 55, "d" should be -- δ --.

Column 35,
Lines 2, 5 and 14, "C." should be -- C --.
Lines 20 and 38, "d" should be -- δ --.
Line 38, "CDCl$_1$" should be -- CDCl$_3$ --.

Signed and Sealed this

Twentieth Day of July, 2004

JON W. DUDAS
*Acting Director of the United States Patent and Trademark Office*